US006359174B1

(12) United States Patent
MacMillan et al.

(10) Patent No.: US 6,359,174 B1
(45) Date of Patent: Mar. 19, 2002

(54) LEWIS ACID-CATALYZED CLAISEN REARRANGEMENT IN THE PREPARATION OF CHIRAL PRODUCTS

(75) Inventors: David W. C. MacMillan; Vy Dong; Tehshik Yoon, all of Pasadena, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/670,863

(22) Filed: Sep. 26, 2000

(51) Int. Cl.$^7$ ...................... C07C 231/02; C07D 265/30
(52) U.S. Cl. ........................................ 564/142; 544/106
(58) Field of Search ........................... 544/106; 564/142

(56) References Cited

PUBLICATIONS

Inokuchi et al, Bull. Chem. Soc. Jpn, vol. 62, 3739–3741, 1989.*
Blechert (1989), "The Hetero–Cope Rearrangement in Organic Synthesis," *Synthesis* 2:71–82.
Corey et al. (1991), "Highly Enantioselective and Diastereoselective Ireland–Claisen Rearrangement of Achiral Allylic Esters," *J. Am. Chem. Soc.* 113(10):4026–4028.
Corey et al. (1995), "Enantioselective Total Synthesis of β–Elemene and Fuscol Based on Enantiocontrolled Ireland–Claisen Rearrangement," *J. Am. Chem. Soc.* 117(1):193–196.
Deur et al. (1996), "Photochemical Reaction Between Tertiary Allylic Amines and Chromium Carbene Complexes: Synthesis of Lactams via a Zwitterion Aza Cope Rearrangement," *J. Org. Chem.* 61(8):2871–2876.
Diederich et al. (1995), "Synthesis of Optically Active Nine–Membered Ring Lactams by a Zwitterionic Aza–Claisen Reaction," *Angew. Chem. Int. Ed. Engl.* 34(9):1026–1028.
Edstrom (1991), "New Methodology for the Synthesis of Functionalized Indolizidine and Quinolizidine Ring Systems," *J. Am. Chem. Soc.* 113(17):6690–6692.
Enders et al. (1996). "Asymmetric [3,3]–Sigmatropic Rearrangements in Organic Synthesis," *Tetrahedron: Asymmetry* 7(7):1847–1882.
Ishida et al. (1989), "A Convenient and Regioselective Synthesis of 4,6–Diaryl–2,3,4,7–Tetrahydrooxepin–2–ones and 1,4–Diphenyl–2,3,4, 7–Tetrahydro–1H–Azepin–2–One," *Synthesis* 7:562–564.
Kallmerten et al. (1989), "Recent Applications of Sigmatropic Reactions to the Synthesis of Highly–Oxygenated Natural Products," *Stud. Nat. Prod. Chem.* 3:233–285.
Kunng et al. (1983), "A Novel Synthetic Approach to Reserpine Based Upon Amino–Claisen Rearrangements of Zwitterionic N–Vinylisoquinuclidenes," *J. Org. Chem.* 48(23):4262–4266.

Malherbe et al. (1978), "A New Type of Claisen Rearrangement Involving 1,3–Dipolar Intermediates," *Helvetica Chimica Acta* 61(295):3096–3099.
Malherbe et al. (1983), "Reactions of Haloketenes With Allyl Ethers and Thioethers: A New Type of Calisen Rearrangement," *J. Org. Chem.* 48(6):860–869.
Maruoka et al. (1990), "Asymmetric Claisen Rearrangement Catalyzed by Chiral Organoaluminum Reagent," *J. Am. Chem. Soc.* 112(21):7791–7793.
Maruoka et al. (1995), "Molecular Design of a Chiral Lewis Acid for the Asymmetric Claisen Rearrangement," *Am. Chem. Soc.* 117(3):1165–1166.
Maruya et al. (1992), "Some Unexpected Reactions Involving Diphenylketene," *J. Chem. Soc. Perkin Trans. 1*:1617–1621.
Moody (1987), "Claisen Rearrangements in Heteroaromatic Systems," *Advances in Heterocyclic Chemistry* 42:203–244.
Mori et al. (1984), "Organoaluminum Assisted Rearrangements of Five–Membered Ring Enol Ethers With Vinyl Substituents," *Tetrahedron* 40(20):4013–4018.
Rosini et al. (1981), "Reaction of Dichloroketene With Cyclic Thioketals of α,β–Cycloalkenones: Synthesis of 1,7–Dithiacycloalk–5–En–2–One Derivatives by a Four–Carbon Cycloenlargement," *J. Org. Chem.* 46(11):2228–2230.
Saito et al. (1996), Aluminum Tris(4–Bromo–2,6–Diphenylphenoxide)(ATPH–Br): An Effective Catalyst for Claisen Rearrangement, *Synlett* 8:720–722.
Stevenson et al. (1982), "A 1,5–Diene Synthesis via Titanium and Aluminum Mediated Reactions," *Tetrahedron Letters* 23(31):3143–3146.
Takai et al. (1981), "Aliphatic Claisen Rearrangement Promoted by Organoaluminium Compounds," *Tetrahedron Letters* 22(40):3985–3988.
Vedejs et al. (1994), "Aza–Claisen Rearrangements Initiated by Acid–Catalyzed Michael Addition," *J. Am. Chem. Soc.* 116(2):579–588.
Yoon et al. (1999), "Development of a New Lewis Acid–Catalyzed Claisen Rearrangement," *J. Am. Chem. Soc.* 121(41):9726–9727.
Ziegler (1988), "The Thermal, Aliphatic Claisen Rearrangement," *Chemical Reviews* 88(8):1423–1452.

* cited by examiner

*Primary Examiner*—Shailendra Kumar
(74) *Attorney, Agent, or Firm*—Dianne E. Reed; Reed & Associates

(57) ABSTRACT

A novel Claisen rearrangement reaction is provided. An allylic reactant such as an allylic amine, an allylic ether or an allylic thioether is reacted with an acid chloride in the presence of a Lewis acid catalyst composition composed of a Lewis acid and a base selected from the group consisting of tertiary amines and non-nitrogenous bases. The stereochemistry of the reaction product is readily controlled by the positioning and size of substituents on the allylic reactant. The reaction may be carried out on a solid support, i.e., on the surface of a substrate suitable for conducting solid phase chemical reactions.

44 Claims, 1 Drawing Sheet

LEWIS ACID-CATALYZED CLAISEN REARRANGEMENT IN THE PREPARATION OF CHIRAL PRODUCTS

TECHNICAL FIELD

The present invention relates generally to synthetic organic chemistry. More particularly, the invention relates to the Claisen rearrangement reaction and to a novel method of performing such reactions so as to give rise to chiral products. The invention finds utility in the fields of organic synthesis and stereospecific catalysis.

BACKGROUND

Since its discovery in 1912, the Claisen rearrangement has become one of the most powerfull tools for carbon-carbon bond formation in chemical synthesis. See, e.g., Claisen (1912) *Chem. Ber.* 45:3157; Enders et al. (1996) *Tetrahedron: Asymmetry* 7:1847; Blechert et al. (1989) *Synthesis* 71; Kallmerten et al. (1989) *Stud. Nat. Prod. Chem.* 3:323; Moody et al. (1987) *Adv. Heterocycl. Chem.* 42:203; and Ziegler et al. (1988) *Chem. Rev.* 88:1423. The Claisen reaction is a [3,3]-sigmatropic rearrangement, which involves the conversion of an allylic compound, generally an allylic vinyl ether, to an α,β-disubstituted, α,γ-unsaturated carbonyl compound. The reaction may be illustrated as follows:

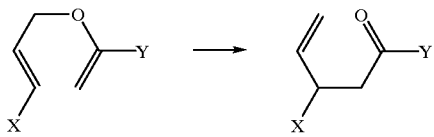

Allylic aryl ethers also undergo a Claisen rearrangement to give ortho-allylphenols:

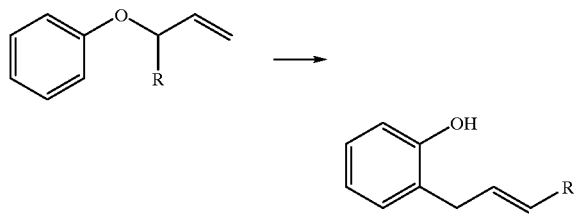

Activation of Claisen reactions has traditionally been accomplished under thermal control, typically at temperatures of 200° C. or more. Activation has also been achieved through the incorporation of cationic or anionic charge in the bond reorganization event (see Takai et al. (1981) *Tetrahedron Lett.* 22:3985; Takai et al. (1984) *Bull. Chem. Soc.* 51:446; Stevenson et al. (1982) *Tetrahedron Lett.* 23:3143; and Takai et al. (1984) *Tetrahedron* 40:4013; Arnold et al. (1949) *J. Am. Chem. Soc.* 21:1150; Ireland et al. (1973) *J. Am. Chem. Soc.* 94:5897; Denmark et al. (1982) *J. Am. Chem. Soc.* 104:4972; Wilson et al. (1984) *J. Org. Chem.* 49:722; Buchi et al. (1985) *J. Org. Chem.* 50:4664; and Alker et al. (1990) *J. Chem. Soc. Perkins Trans.* 1, 1623). Despite its prolific use in chemical synthesis, very few examples of catalytic Claisen variants have been reported. See Vedejs et al. (1994) *J. Am. Chem. Soc.* 116:579, pertaining to protic acid (e.g., toluenesulfonic acid) catalysis of a Michael addition reaction, in turn initiating an aza-Claisen rearrangement. See also Saito et al. (1996) *Synlett*, 720, which describes the use of an aluminum catalyst, aluminum tris(4-bromo-2,6-diphenylphenoxide), in the Claisen rearrangement of allyl vinyl ethers.

In 1978, Bellus and Malherbe reported a ketene-Claisen reaction, in which treatment of an allyl ether with dichloroketene was found to result in the formation of a 1,3-dipolar allyl vinyl ether, which subsequently underwent [3,3]-bond reorganization, as follows:

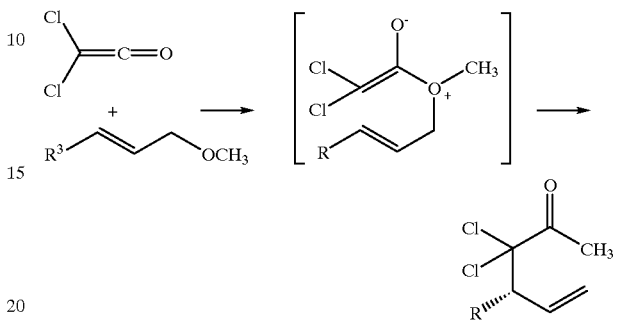

(Malherbe et al. (1978) *Helv. Chim. Acta* 61:3096; Malherbe et al. (1983) *J. Org. Chem.* 48:860). Subsequently, others have demonstrated utility of tertiary allylic amines in analogous [3,3]-sigmatropic rearrangement reactions. Edstrom et al. (1991) *J. Am. Chem. Soc.* 113:6690; Kunng et al. (1983) *J. Org. Chem.* 48:4262; Maruya et al. (1992) *J. Chem. Soc., Perkin Trans*, 1617; Vedejs et al., supra; Diederich et al. (1995) *Angew Chem., Int. Ed. Engl.* 34:1026; Deur et al. (1996) *J. Org. Chem.* 61:2871).

The aforementioned reactions are limited because of the ketene reactant used, as ketenes are highly unstable compounds. Furthermore, prior syntheses are generally not enantioselective; those who have attempted enantioselective Claisen rearrangements have met with substantial difficulties. For example, Corey et al. (1996) *J. Am. Chem. Soc.* 118:1229, developed an enantioselective Claisen reaction of an allylic ester, but the synthesis was not catalytic and required a reaction time of fourteen days. Yamamoto et al. (1995) *J. Am. Chem. Soc.* 117:1165, also developed an enantioselective Claisen reaction for rearrangement of an allylic vinyl ether, but the synthesis required stoichiometric quantities of an aluminum promoter.

Accordingly, there is a need in the art for an improved Claisen reaction that proceeds quickly, can be conducted as a "one-pot" synthesis, is activated using catalytic quantities of a catalytic composition, and can be used to produce chiral products in enantiomerically pure form.

SUMMARY OF THE INVENTION

It is therefore a primary object of the invention to provide an improved Claisen reaction which addresses the aforementioned need in the art.

It is another object of the invention to provide a method for conducting a Claisen rearrangement reaction by reacting an allylic compound with an acid chloride in the presence of a Lewis acid catalyst composition.

It is still another object of the invention to provide such a method wherein the allylic compound is an allylic tertiary amine.

It is yet another object of the invention to provide such a method wherein one of the reactants is covalently linked, either directly or indirectly, to the surface of a solid support.

It is a further object of the invention to provide such a method wherein the position and/or size of substituents on the allylic reactant determine the stereochemistry of the reaction product.

Additional objects, advantages and novel features of the invention will be set forth in part in the description which follows, and in part will become apparent to those skilled in the art upon examination of the following, or may be learned by practice of the invention.

In one embodiment, then, the invention provides a method for conducting a Claisen rearrangement reaction via Lewis acid catalysis. The method involves reaction of an acid chloride with an allylic reactant (typically an allylic amine, an allylic ether, or an allylic thioether) in the presence of a Lewis acid catalyst composition comprised of two catalyst components, a first component composed of a Lewis acid, and a second component composed of a base, either a tertiary amine or a non-nitrogenous base. The reaction is conducted under inert, nonaqueous conditions at a temperature typically in the range of approximately −110° C. to 200° C., and can give rise to a nonracemic, chiral product. The reaction is represented in Scheme 1:

SCHEME 1

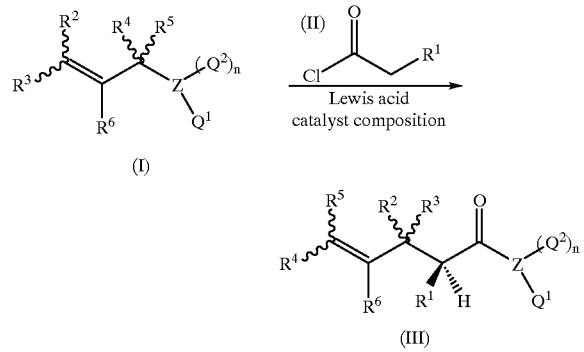

In compounds (I), (II) and (III), the various substituents are as follows:

$R^1$, $R^2$, $R^3$, $R^4$, $R^5$ and $R^6$ are independently selected from the group consisting of hydrido, halo, hydroxyl, sulfhydryl, amino, substituted amino, hydrocarbyl, substituted hydrocarbyl, heteroatom-containing hydrocarbyl, and substituted heteroatom-containing hydrocarbyl;

Z is N, O or S;

n is zero or 1, with the proviso that when Z is N, n is 1, and when Z is O or S, n is zero; and $Q^1$ and $Q^2$ are independently selected from the group consisting of hydrocarbyl, substituted hydrocarbyl, heteroatom-containing hydrocarbyl, and substituted heteroatom-containing hydrocarbyl, or, when Z is N and n is 1, $Q^1$ and $Q^2$ may be joined together in a ring structure, generally a five- or six-membered cyclic group, or may together with Z form an azide —$N_3$.

The stereochemistry of the product is controlled by the position and/or size of the substituents $R^2$, $R^3$, $R^4$ and $R^5$ on the allylic reactant. The process enables preparation of a wide variety of stereospecific compounds useful, for example, as starting materials in the synthesis of natural products and polymers, as pharmaceutical agents, as agrochemical agents, and as in combinatorial processes wherein arrays of chemical reactions are carried out in parallel on a solid support.

DETAILED DESCRIPTION OF THE INVENTION

Figure 1:
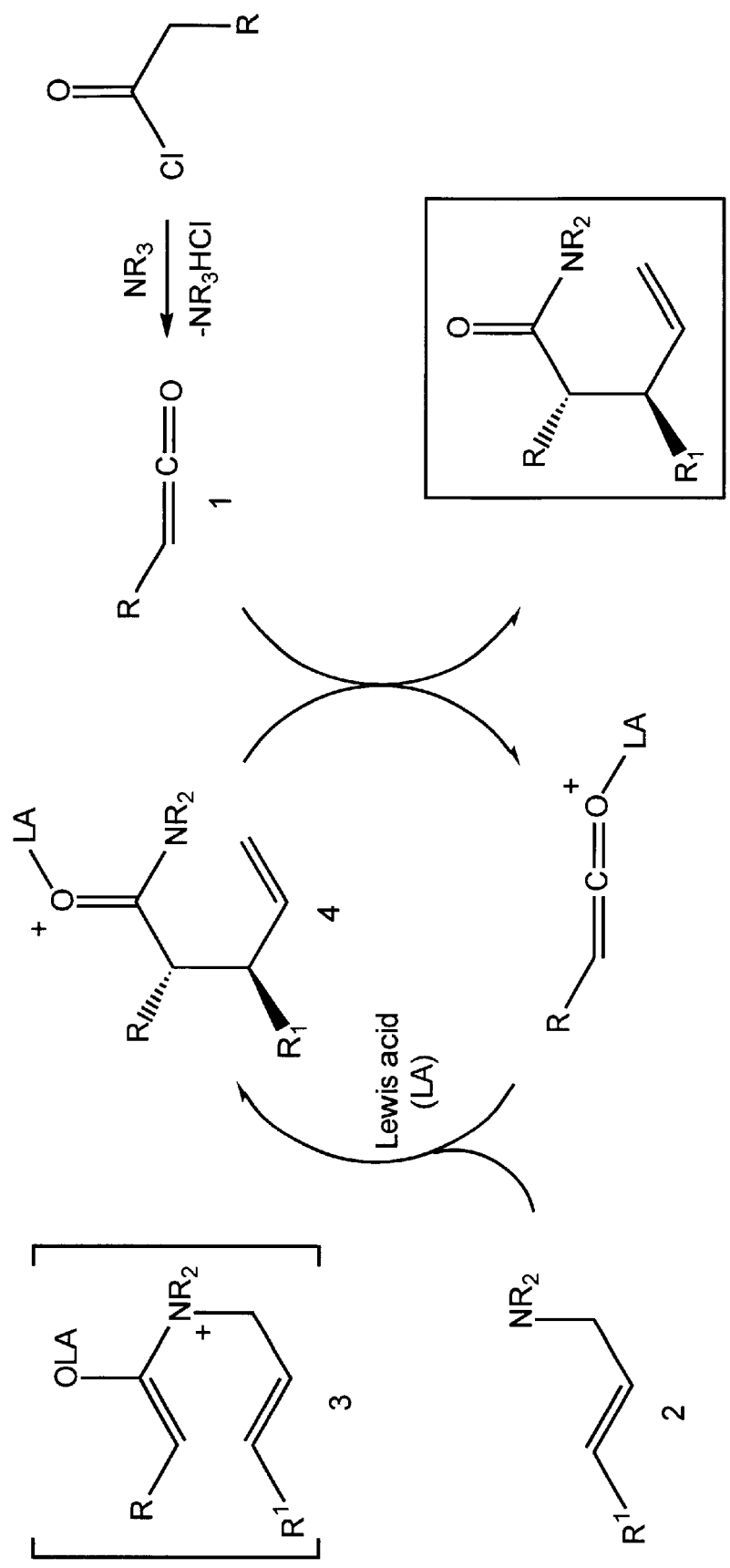
FIG. 1 schematically illustrates the Lewis acid catalyzed Claisen rearrangement reactions conducted in the Examples herein.

It is to be understood that unless otherwise indicated this invention is not limited to specific reactants, catalyst compositions, or synthetic methods. It is also to be understood that the terminology used herein is for the purpose of describing particular embodiments only, and is not intended to be limiting.

As used in this specification and the appended claims, the singular forms "a," "an" and "the" include plural referents unless the context clearly dictates otherwise. Thus, reference to reference to "a Lewis acid" includes mixtures of Lewis acids, "a catalyst composition" includes mixtures of catalyst compositions, and the like.

In describing and claiming the present invention, the following terminology will be used in accordance with the definitions set out below.

The following definitions pertain to chemical structures, molecular segments and substituents:

As used herein, the phrase "having the structure" is not intended to be limiting and is used in the same way that the term "comprising" is commonly used. The term "independently selected from the group consisting of" is used herein to indicate that the recited elements, e.g., R groups or the like, can be identical or different.

"Optional" or "optionally" means that the subsequently described event or circumstance may or may not occur, and that the description includes instances where said event or circumstance occurs and instances where it does not. For example, the phrase "optionally substituted hydrocarbyl" means that a hydrocarbyl moiety may or may not be substituted and that the description includes both unsubstituted hydrocarbyl and hydrocarbyl where there is substitution.

The term "alkyl" as used herein refers to a branched or unbranched saturated hydrocarbon group typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although again not necessarily, alkyl groups herein contain 1 to about 12 carbon atoms. The term "lower alkyl" intends an alkyl group of one to six carbon atoms, preferably one to four carbon atoms. "Substituted alkyl" refers to alkyl substituted with one or more substituent groups, and the terms "heteroatom-containing alkyl" and "heteroalkyl" refer to alkyl in which at least one carbon atom is replaced with a heteroatom.

The term "alkenyl" as used herein refers to a branched or unbranched hydrocarbon group typically although not necessarily containing 2 to about 24 carbon atoms and at least one double bond, such as ethenyl, n-propenyl, isopropenyl, s-propenyl, 2-propenyl, n-butenyl, isobutenyl, octenyl, decenyl, and the like. Generally, although again not necessarily, alkenyl groups herein contain 2 to about 12 carbon atoms. The term "lower alkenyl" intends an alkenyl group of two to six carbon atoms, preferably two to four carbon atoms. "Substituted alkenyl" refers to alkenyl substituted with one or more substituent groups, and the terms "heteroatom-containing alkenyl" and "heteroalkenyl" refer to alkenyl in which at least one carbon atom is replaced with a heteroatom.

The term "alkynyl" as used herein refers to a branched or unbranched hydrocarbon group typically although not necessarily containing 2 to about 24 carbon atoms and at least one triple bond, such as ethynyl, n-propynyl, n-butynyl, octynyl, decynyl, and the like. Generally, although again not necessarily, alkynyl groups herein contain 2 to about 12 carbon atoms. The term "lower alkynyl" intends an alkynyl group of two to six carbon atoms, preferably 2, 3 or 4 carbon atoms. "Substituted alkynyl" refers to alkynyl substituted with one or more substituent groups, and the terms "heteroatom-containing alkynyl" and "heteroalkynyl" refer to alkynyl in which at least one carbon atom is replaced with a heteroatom.

The term "alkoxy" as used herein intends an alkyl group bound through a single, terminal ether linkage; that is, an "alkoxy" group may be represented as —O-alkyl where "alkyl" is as defined above. A "lower alkoxy" group intends an alkoxy group containing one to six, more preferably one to four, carbon atoms.

Similarly, the term "alkyl thio" as used herein intends an alkyl group bound through a single, terminal thioether linkage; that is, an "alkyl thio" group may be represented as —S-alkyl where "alkyl" is as defined above. A "lower alkyl thio" group intends an alkyl thio group containing one to six, more preferably one to four, carbon atoms.

The term "allenyl" is used herein in the conventional sense to refer to a molecular segment having the structure —CH=C=CH$_2$. An "allenyl" group may be unsubstituted or substituted with one or more non-hydrogen substituents.

The term "aryl" as used herein, and unless otherwise specified, refers to an aromatic substituent containing a single aromatic ring or multiple aromatic rings that are fused together, linked covalently, or linked to a common group such as a methylene or ethylene moiety. The common linking group may also be a carbonyl as in benzophenone, an oxygen atom as in diphenylether, or a nitrogen atom as in diphenylamine. Preferred aryl groups contain one aromatic ring or two fused or linked aromatic rings, e.g., phenyl, naphthyl, biphenyl, diphenylether, diphenylamine, benzophenone, and the like. In particular embodiments, aryl substituents have 1 to about 200 carbon atoms, typically 1 to about 50 carbon atoms, and preferably 1 to about 20 carbon atoms. "Substituted aryl" refers to an aryl moiety substituted with one or more substituent groups, and the terms "heteroatom-containing aryl" and "heteroaryl" refer to aryl in which at least one carbon atom is replaced with a heteroatom.

The term "aralkyl" refers to an alkyl group with an aryl substituent, and the term "aralkylene" refers to an alkylene group with an aryl substituent; the term "alkaryl" refers to an aryl group that has an alkyl substituent, and the term "alkarylene" refers to an arylene group with an alkyl substituent.

The terms "halo" and "halogen" are used in the conventional sense to refer to a chloro, bromo, fluoro or iodo substituent. The terms "haloalkyl," "haloalkenyl" or "haloalkynyl" (or "halogenated alkyl," "halogenated alkenyl," "halogenated aromatic" or "halogenated alkynyl") refers to an alkyl, alkenyl, aromatic or alkynyl group, respectively, in which at least one of the hydrogen atoms in the group has been replaced with a halogen atom.

The term "heteroatom-containing" as in a "heteroatom-containing hydrocarbyl group" refers to a molecule or molecular fragment in which at least one carbon atom is replaced with an atom other than carbon, e.g., nitrogen, oxygen, sulfur, phosphorus or silicon. Similarly, the term "heteroalkyl" refers to an alkyl substituent that is heteroatom-containing, the term "heterocyclic" refers to a cyclic substituent that is heteroatom-containing, the term "heteroaryl" refers to an aryl substituent that is heteroatom-containing, and the like. When the term "heteroatom-containing" appears prior to a list of possible heteroatom-containing groups, it is intended that the term apply to every member of that group. That is, the phrase "heteroatom-containing alkyl, alkenyl and alkynyl" is to be interpreted as "heteroatom-containing alkyl, heteroatom-containing alkenyl and heteroatom-containing alkynyl."

"Hydrocarbyl" refers to univalent hydrocarbyl radicals containing 1 to about 30 carbon atoms, preferably 1 to about 24 carbon atoms, most preferably 1 to about 12 carbon atoms, including branched or unbranched, saturated or unsaturated species, such as alkyl groups, alkenyl groups, aryl groups, and the like. The term "lower hydrocarbyl" intends a hydrocarbyl group of one to six carbon atoms, preferably one to four carbon atoms. The term "hydrocarbylene" intends a divalent hydrocarbyl moiety containing 1 to about 30 carbon atoms, preferably 1 to about 24 carbon atoms, most preferably 1 to about 12 carbon atoms, including branched or unbranched, saturated or unsaturated species, or the like. The term "lower hydrocarbylene" intends a hydrocarbylene group of one to six carbon atoms, preferably one to four carbon atoms. "Substituted hydrocarbyl" refers to hydrocarbyl substituted with one or more substituent groups, and the terms "heteroatom-containing hydrocarbyl" and "heterohydrocarbyl" refer to hydrocarbyl in which at least one carbon atom is replaced with a heteroatom. Similarly, "substituted hydrocarbylene" refers to hydrocarbylene substituted with one or more substituent groups, and the terms "heteroatom-containing hydrocarbylene" and "heterohydrocarbylene" refer to hydrocarbylene in which at least one carbon atom is replaced with a heteroatom.

A "Lewis acid" refers to any species with a vacant orbital, in contrast to a "Lewis base," which refers to a compound with an available pair of electrons, either unshared or in a π-orbital. Typically, a Lewis acid refers to a compound containing an element that is two electrons short of having a complete valence shell.

By "substituted" as in "substituted hydrocarbyl," "substituted hydrocarbylene," "substituted alkyl," "substituted alkenyl" and the like, as alluded to in some of the aforementioned definitions, is meant that in the hydrocarbyl, hydrocarbylene, alkyl, alkenyl or other moiety, at least one hydrogen atom bound to a carbon atom is replaced with one or more substituents that are functional groups such as hydroxyl, alkoxy, thio, amino, halo, silyl, and the like. When the term "substituted" appears prior to a list of possible substituted groups, it is intended that the term apply to every member of that group. That is, the phrase "substituted alkyl, alkenyl and alkynyl" is to be interpreted as "substituted alkyl, substituted alkenyl and substituted alkynyl." Similarly, "optionally substituted alkyl, alkenyl and alkynyl" is to be interpreted as "optionally substituted alkyl, optionally substituted alkenyl and optionally substituted alkynyl."

The term "amino" is used herein to refer to the —NH$_2$ group, while "substituted amino" refers to —NZ$^1$Z$^2$ groups, where each of Z$^1$ and Z$^2$ is independently selected from the group consisting of optionally substituted hydrocarbyl and heteroatom-containing hydrocarbyl, or wherein Z$^1$ and Z$^2$ are linked to form an optionally substituted hydrocarbylene or heteroatom-containing hydrocarbylene bridge.

The term "sulfhydryl" is used herein to refer to the —SH group, while "thio" is used herein to refer to the group —SZ$^1$, where Z$^1$ is selected from the group consisting of optionally substituted hydrocarbyl and hetero-containing hydrocarbyl. A compound containing a sulfur atom bound to two $Z^1$ moieties is termed a "thioether."

The term "sulfhydryl" refers to a structure that does not have an improper rotation axis ($S_n$), i.e., it belongs to point group $C_n$ or $D_n$. Such molecules are thus chiral with respect to an axis, plane or center of asymmetry. Preferred "chiral" molecules herein are in enantiomerically pure form, such that a particular chiral molecule represents at least about 95 wt. % of the composition in which it is contained, more preferably at least about 99 wt. % of that composition.

The term "enantioselective" refers to a chemical reaction that preferentially results in one enantiomer relative to a second enantiomer, i.e., gives rise to a product in which one enantiomer represents at least about 51 wt. % of the product. Preferably, in the enantioselective reactions herein, the selectively favored enantiomer represents at least about 85 wt. % of the product, optimally at least about 95 wt. % of the product.

As used herein all reference to the elements and groups of the Periodic Table of the Elements is to the version of the table published by the Handbook of Chemistry and Physics, CRC Press, 1995, which sets forth the new IUPAC system for numbering groups. In the chemical structures herein, the use of bold and dashed lines to denote particular conformation of groups again follows APACE convention. The symbols "α" and "β" indicate the specific stereochemical configuration of a substituent at an asymmetric carbon atom in a chemical structure as drawn. Thus "α," denoted by a broken line, indicates that the group in question is below the general plane of the molecule as drawn, and "β," denoted by a bold line, indicates that the group in question is above the general plane of the molecule as drawn. The bond symbol

∿∿∿ refers to a covalent bond that may be either α or β.

In one embodiment, then, the invention provides a method for conducting a Claisen rearrangement reaction via Lewis acid catalysis. The method involves reaction of an acid chloride with an allylic reactant (typically an allylic amine, an allylic ether or an allylic thioether) in the presence of a Lewis acid catalyst composition comprised of two catalyst components, a first component composed of a Lewis acid, and a second component composed of a base, either a tertiary amine or a non-nitrogenous base. The reaction is conducted under inert, nonaqueous conditions at a temperature typically in the range of approximately –110° C. to 200° C., and can give rise to a nonracemic, chiral product. As will be explained in further detail, the stereochemistry of the reaction product is readily controlled by the stereochemistry of the allylic amine.

The reaction proceeds according to Scheme 1:

SCHEME 1

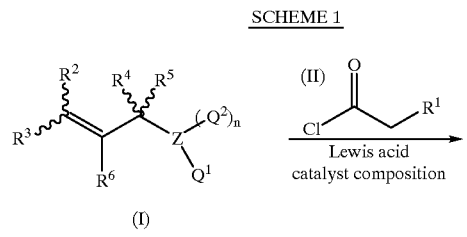

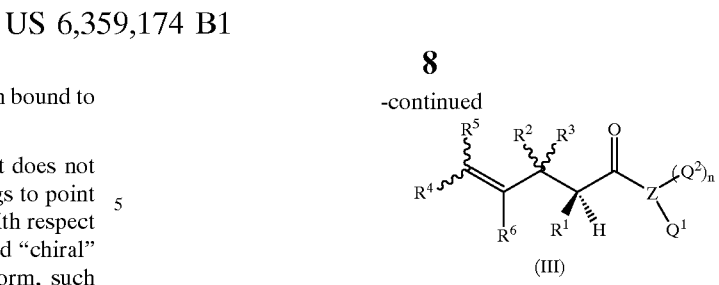

While not wishing to be bound by theory, it is proposed that the allylic reactant (I) acts to convert the acid chloride (II) to a ketene intermediate $R^1$=C=O, which then undergoes a rearrangement reaction with the allylic reactant (see FIG. 1). In the acid chloride and the allylic reactant, the various substituents are as follows:

$R^1$, $R^2$, $R^3$, $R^4$, $R^5$ and $R^6$ are independently selected from the group consisting of hydrido, halo, hydroxyl, sulfhydryl, amino, substituted amino, hydrocarbyl (e.g., alkyl, alkenyl, alkynyl, aryl, alkaryl, aralkyl, etc.), substituted hydrocarbyl (e.g., substituted alkyl, alkenyl, alkynyl, aryl, alkaryl, aralkyl, etc.), heteroatom-containing hydrocarbyl (e.g., heteroatom-containing alkyl, alkenyl, alkynyl, aryl, alkaryl, aralkyl, etc.), and substituted heteroatom-containing hydrocarbyl (e.g., substituted heteroatom-containing alkyl, alkenyl, alkynyl, aryl, alkaryl, aralkyl, etc.). $R^2$ and $R^4$ may also be linked to form a six-membered ring.

Z is N, O or S, and n is zero or 1, with the proviso that when Z is N, n is 1, and when Z is O or S, n is zero. Therefore, the allylic reactant (I) is either an allylic amine (i.e., an allylic tertiary amine), an allylic ether, or an allylic thioether.

$Q^1$ and $Q^2$ are independently selected from the group consisting of hydrocarbyl (e.g., alkyl, alkenyl, alkynyl, aryl, alkaryl, aralkyl, etc.), substituted hydrocarbyl (e.g., substituted alkyl, alkenyl, alkynyl, aryl, alkaryl, aralkyl, etc.), heteroatom-containing hydrocarbyl (e.g., heteroatom-containing alkyl, alkenyl, alkynyl, aryl, alkaryl, aralkyl, etc.), substituted heteroatom-containing hydrocarbyl (e.g., substituted heteroatom-containing alkyl, alkenyl, alkynyl, aryl, alkaryl, aralkyl, etc.), or, when Z is N and n is 1, $Q^1$ and $Q^2$ may be joined together in a ring structure, generally a five- or six-membered cyclic group such as piperidinyl, piperazinyl, pyrrolidinyl, imidazolidinyl, morpholino, or the like, or $Q^1$ and $Q^2$ may together with Z form an azide group —$N_3$.

In a preferred embodiment, the allylic reactant is an allylic tertiary amine, such that the moiety Z is a nitrogen atom and n is 1. Preferred allylic tertiary amines have the structure (IV)

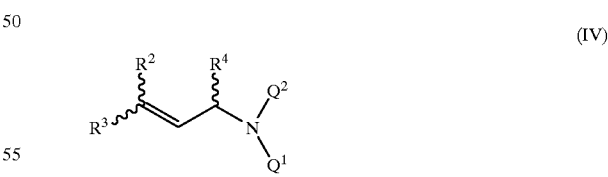

wherein $R^2$, $R^3$ and $R^4$ are as defined above, and $Q^1$ and $Q^2$ are joined together to form a five- or six-membered cyclic group, e.g., piperidinyl, piperazinyl, pyrrolidinyl, imidazolidinyl, morpholino, or the like, or together with the nitrogen atom shown form an azide —$N_3$. Examples of suitable allylic tertiary amines include, but are not limited to, the following:

4-prop-2-enylmorpholine;
prop-2-enylpiperidine;
prop-2-enylpiperazine;

prop-2-enylpyrrolidine;
prop-2-enylimidazolidine;
prop-2-enylazide;
4-((2E)but-2-enyl)morpholine;
((2E)but-2-enyl)piperidine;
((2E)but-2-enyl)piperazine;
((2E)but-2-enyl)pyrrolidine;
((2E)but-2-enyl)imidazolidine;
((2E)but-2-enyl)azide;
4-((2E)-1-methylbut-2-enyl)morpholine;
((2E)-1-methylbut-2-enyl)piperidine;
((2E)-1-methylbut-2-enyl)piperazine;
((2E)-1-methylbut-2-enyl)pyrrolidine;
((2E)-1-methylbut-2-enyl)imidazolidine;
((2E)-1-methylbut-2-enyl)azide;
4-((2E)-2-ethylbut-2-enyl)morpholine;
((2E)-2-ethylbut-2-enyl)piperidine;
((2E)-2-ethylbut-2-enyl)piperazine;
((2E)-2-ethylbut-2-enyl)pyrrolidine;
((2E)-2-ethylbut-2-enyl)imidazolidine;
((2E)-2-ethylbut-2-enyl)azide;
4-[(2E)-2-benzylbut-2-enyl]morpholine;
[(2E)-2-benzylbut-2-enyl]piperidine;
[(2E)-2-benzylbut-2-enyl]piperazine;
(2E)-2-benzylbut-2-enyl]pyrrolidine;
(2E)-2-benzylbut-2-enyl]imidazolidine;
(2E)-2-benzylbut-2-enyl]azide;
4-((2E)-3-methylpent-2-enyl)morpholine;
((2E)-3-methylpent-2-enyl)piperidine;
((2E)-3-methylpent-2-enyl)piperazine;
((2E)-3-methylpent-2-enyl)pyrrolidine;
((2E)-3-methylpent-2-enyl)imidazolidine;
((2E)-3-methylpent-2-enyl)azide;
4-((2E)-3-chloroprop-2-enyl)morpholine;
((2E)-3-chloroprop-2-enyl)piperidine;
((2E)-3-chloroprop-2-enyl)piperazine;
((2E)-3-chloroprop-2-enyl)pyrrolidine;
(2E)-3-chloroprop-2-enyl)imidazolidine;
(2E)-3-chloroprop-2-enyl)azide;
4-((2Z)but-2-enyl)morpholine;
((2Z)but-2-enyl)piperidine;
((2Z)but-2-enyl)piperazine;
((2Z)but-2-enyl)pyrrolidine;
((2Z)but-2-enyl)imidazolidine;
((2Z)but-2-enyl)azide;
4-((2Z)-1-methylbut-2-enyl)morpholine;
((2Z)-1-methylbut-2-enyl)piperidine;
((2Z)-1-methylbut-2-enyl)piperazine;
((2Z)-1-methylbut-2-enyl)pyrrolidine;
((2Z)-1-methylbut-2-enyl)imidazolidine;
((2Z)-1-methylbut-2-enyl)azide;
4-((2Z)-2-ethylbut-2-enyl)morpholine;
((2Z)-2-ethylbut-2-enyl)piperidine;
((2Z)-2-ethylbut-2-enyl)piperazine;
((2Z)-2-ethylbut-2-enyl)pyrrolidine;
((2Z)-2-ethylbut-2-enyl)imidazolidine;
((2Z)-2-ethylbut-2-enyl)azide;
4-[(2Z)-2-benzylbut-2-enyl]morpholine;
[(2Z)-2-benzylbut-2-enyl]piperidine;
[(2Z)-2-benzylbut-2-enyl]piperazine;
[(2Z)-2-benzylbut-2-enyl]pyrrolidine;
[(2Z)-2-benzylbut-2-enyl]imidazolidine;
[(2Z)-2-benzylbut-2-enyl]azide;
4-((2Z)-3-methylpent-2-enyl)morpholine;
((2Z)-3-methylpent-2-enyl)piperidine;
((2Z)-3-methylpent-2-enyl)piperazine;
((2Z)-3-methylpent-2-enyl)pyrrolidine;
(2Z)-3-methylpent-2-enyl)imidazolidine;
(2Z)-3-methylpent-2-enyl)azide;
4-((2Z)-3-chloroprop-2-enyl)morpholine;
((2Z)-3-chloroprop-2-enyl)piperidine;
((2Z)-3-chloroprop-2-enyl)piperazine;
((2Z)-3-chloroprop-2-enyl)pyrrolidine;
((2Z)-3-chloroprop-2-enyl)imidazolidine; and
((2Z)-3-chloroprop-2-enyl)azide.

The acid chloride (I) may be any acid chloride that is suitable for undergoing the rearrangement reaction with the allylic reactant (II) as illustrated in Scheme 1. $R^1$, as noted earlier herein, is hydrido, halo, hydroxyl, sulfhydryl, amino, substituted amino, hydrocarbyl (e.g., alkyl, alkenyl, alkynyl, aryl, alkaryl, aralkyl, etc.), substituted hydrocarbyl (e.g., substituted alkyl, alkenyl, alkynyl, aryl, alkaryl, aralkyl, etc.), heteroatom-containing hydrocarbyl (e.g., heteroatom-containing alkyl, alkenyl, alkynyl, aryl, alkaryl, aralkyl, etc.), or substituted heteroatom-containing hydrocarbyl (e.g., substituted heteroatom-containing alkyl, alkenyl, alkynyl, aryl, alkaryl, aralkyl, etc.), and is preferably hydrocarbyl, substituted hydrocarbyl, heteroatom-containing hydrocarbyl, or substituted heteroatom-containing hydrocarbyl. Most preferably, $R^1$ is alkyl (with lower alkyl substituents such as methyl being optimal), benzyloxy or thiophenyl.

Examples of suitable acid chlorides thus include, but are not limited to, propanoyl chloride, 2-methylpropanoyl chloride, 2-ethylpropanoyl chloride, 2-cyclohexylpropanoyl chloride, 2-phenylpropanoyl chloride, butanoyl chloride, 2-methylbutanoyl chloride, 2-ethylbutanoyl chloride, 2-cyclohexylbutanoyl chloride, 2-phenylbutanoyl chloride, 3-methylbutanoyl chloride, 3-ethylbutanoyl chloride, 3-cyclohexylbutanoyl chloride, 3-phenylbutanoyl chloride, 2-(phenylmethoxy)acetyl chloride, 2-(p-methylphenylmethoxy)acetylchloride, 2-(p-ethylphenylmethoxy)acetylchloride, 2-(p-nitrophenylmethoxy)acetylchloride, 2-(o-methylphenylmethoxy)acetylchloride, 2-(o-ethylphenylmethoxy)acetylchloride, 2-(o-nitrophenylmethoxy)acetylchloride, 2-phenylthioacetyl chloride, 2-(o-ethylphenyl)thioacetyl chloride, 2-(m-methylphenylmethoxy)acetylchloride, 2-(o-ethylphenylmethoxy)acetylchloride, 2-(m-nitrophenylmethoxy)acetylchloride, 2-phenylthioacetyl chloride, 2-(p-ethylphenyl)thioacetyl chloride, 2-(p-ethylphenyl)thioacetyl chloride, 2-p-nitrophenyl)thioacetyl chloride, 2-(o-methylphenyl)thioacetyl chloride, 2-(o-ethylphenyl)thioacetyl chloride, 2-(o-nitrophenyl)thioacetyl chloride, 2-(m-methylphenyl)thioacetyl chloride, 2-(m-ethylphenyl)thioacetyl chloride, 2-(m-nitrophenyl) thioacetyl chloride, and the like.

The catalyst composition comprises two catalyst components, a first component composed of a Lewis acid, and a second component composed of a base, either a tertiary amine or a non-nitrogenous base. Suitable Lewis acids generally have the structural formula (V)

$$M(X)_a(Y)_b \qquad\qquad (V)$$

wherein M is a metal, X is halide or halide-containing (e.g., $SbF_6^-$, $BF_4^-$), or is lower alkoxy, fluorinated lower alkoxy (e.g., $OCF_3$, $OCF_2CF_3$, $OCH_2CF_3$), sulfate, acetate, trifluoroacetate, or triflate (i.e., trifluoromethylsulfonate, or $-OSO_2CF_3$), Y is hydrocarbyl, substituted hydrocarbyl, heteroatom-containing hydrocarbyl, substituted heteroatom-containing hydrocarbyl, or an oxygen-containing or nitrogen-containing organic ligand, a is an integer of 1 or more, and the sum of a and b is in the range of 2 to $n_{max}$, where $n_{max}$ is the number of atoms that can bind to M through single covalent or coordination bonds. However, if Y is a bidentate (or multidentate) ligand, obviously it will be the sum of a and 2b (or xb, where x is the number of covalent or coordination bonds linking Y to M) that is in the range of 2 to $n_{max}$. For example, for titanium (M) having two chloro (X) substituents, a single bidentate ligand Y or two monodentate ligands Y may be present, insofar as $n_{max}$, for titanium is 4, and a, by virtue of the two chloro substituents, is 2. Thus, in the foregoing example, for a monodentate ligand Y, b will be (2 to $n_{max}$)−a, i.e., zero to 2, while for a bidentate ligand Y, b will be ½ ((2 to $n_{max}$)−a), i.e., zero or 1.

The metal M may be any metal in the Periodic Table of the Elements. Preferably, the metal is selected from the group consisting of Groups 2 through 13 of the Periodic Table of the Elements and the lanthanides. More preferred metals are Ti, Mg, Al, Sc, Y, Ni, Cu, Zn and Yb, and most preferred metals are Ti, Mg and Al.

Preferred X moieties are halide and triflate. Thus, X may be chloro, bromo, fluoro or iodo, but is typically chloro or bromo, and most preferably is chloro. Y may be, for example, alkyl, particularly lower alkyl (e.g., methyl, ethyl, n-propyl, isopropyl, n-butyl, s-butyl, t-butyl, etc.), aryl (e.g., phenyl, benzyl), aryloxy (e.g., benzyloxy), or the like, or may be a nitrogen-containing or oxygen-containing organic ligand. One example of a suitable oxygen-containing organic ligand is tetrakis-3,5-bis(trifluoromethyl)-phenylborate, commonly referred to as "BARF." Exemplary nitrogen-containing ligands are unsaturated nitrogen-containing ligands such as (VIa) and (VIb)

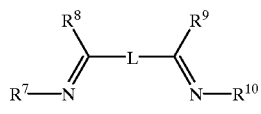
(VIa)

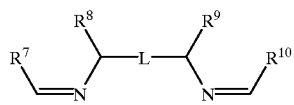
(VIb)

wherein L is a hydrocarbylene, substituted hydrocarbylene, heteroatom-containing hydrocarbylene, substituted heteroatom-containing hydrocarbylene or heteroatom linkage, $R^7$, $R^8$, $R^9$ and $R^{10}$ are as defined for $R^1$ through $R^6$, and wherein $R^7$ and $R^8$ and/or $R^9$ and $R^{10}$ may be linked to form a hydrocarbylene, substituted hydrocarbylene, heteroatom-containing hydrocarbylene, or substituted heteroatom-containing hydrocarbylene bridge. Preferred subsets of such ligands have the structure (VIIa) and (VIIb)

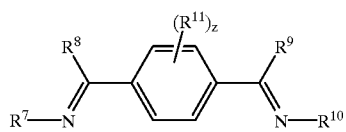
(VIIa)

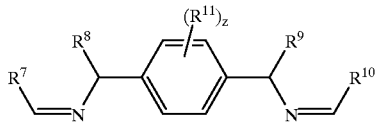
(VIIb)

wherein $R^{11}$ is as defined for $R^7$, $R^8$ and $R^9$, and z is an integer in the range of zero to 5 inclusive. Such ligands include, for example, those having the structural formula (VIII), wherein $R^{12}$, $R^{13}$, $R^{14}$ and $R^{15}$ defined as for $R^{11}$, with one specific such ligand, 4-[2-(3,4-dichlorophenyl)(1,3-oxazolin-4-yl)]-1-methoxybenzene, shown in structural formula (IX).

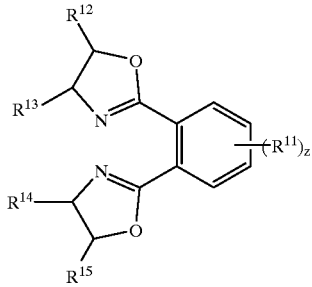
(VIII)

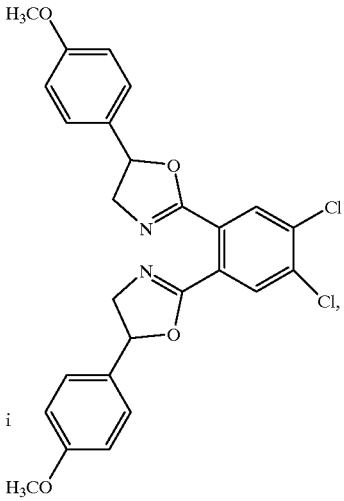
(IX)

in which case a corresponding titanium catalyst component might have the structural formula (X)

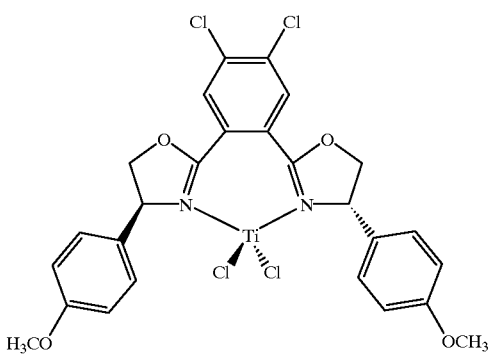
(X)

The second component of the catalyst composition is a base, either a tertiary amine or a non-nitrogenous base. Tertiary amines will have the structure $NR^{16}R^{17}R^{18}$ wherein $R^{16}$, $R^{17}$ and $R^{18}$ are independently hydrocarbyl, substituted hydrocarbyl, heteroatom-containing hydrocarbyl or substituted heteroatom-containing hydrocarbyl, or wherein two of $R^{16}$, $R^{17}$ and $R^{18}$ are linked to form a hydrocarbylene, substituted hydrocarbylene, heteroatom-containing hydrocarbylene or substituted heteroatom-containing hydrocarbylene bridge. Preferred $R^{16}$, $R^{17}$ and $R^{18}$ substituents are alkyl, e.g., lower alkyl. Other useful tertiary amines are nitrogen-containing heterocycles in which at least one nitrogen heteroatom is in the form —N=, as in, for example, pyridine. Examples of tertiary amines suitable as the second catalyst component thus include, but are not limited to, trimethylamine, triethylamine, methyldiethylamine, ethyldimethylamine, methyldiisopropylamine, dimethylisopropylamine, ethyldiisopropylamine, diethylisopropylamine, N-methylpyrrolidine, N-vinylpyrrolidine, N-methylpyridazine, N-methylmorpholine, pyridine, 4-dimethylaminopyridine, 2,6-di-t-butyl-4-methylpyridine, N-methylimidazole, etc.

Non-nitrogenous bases that may serve as the second component of the catalyst composition include, without limitation, inorganic hydroxides, inorganic oxides, and metal carbonates. Inorganic hydroxides include, for example, ammonium hydroxide, alkali metal hydroxide and alkaline earth metal hydroxides, such as sodium hydroxide, calcium hydroxide, potassium hydroxide, magnesium hydroxide, and the like. Inorganic oxides include, for example, magnesium oxide, calcium oxide, and the like. Metal carbonates include sodium carbonate and potassium carbonate. Preferred non-nitrogenous bases are metal hydroxides such as sodium and potassium hydroxide and metal carbonates such as sodium and potassium carbonate.

The reaction method makes possible the preparation of reaction products having a specific and predetermined stereochemistry. That is, such reaction products are "chiral" compounds, which may be obtained in enantiomerically pure form. The stereochemistry of the product, i.e., the positioning of $R^2$, $R^3$, $R^4$ and $R^5$ in the reaction product (III)

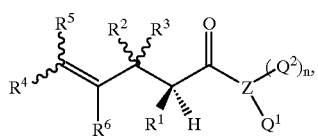
(III)

is determined by the positioning or size of those substituents in the allylic reactant. That is, in the allylic reactants having the structure (I)

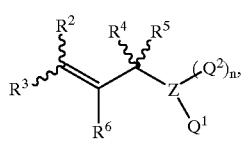
(I)

either (a) $R^2$ is cis and $R^3$ is trans to the carbon atom bound to $R^6$, or (b) the converse is true, i.e., $R^2$ is trans and $R^3$ is cis to the carbon atom bound to $R^6$. The former compounds have the structure (Ia)

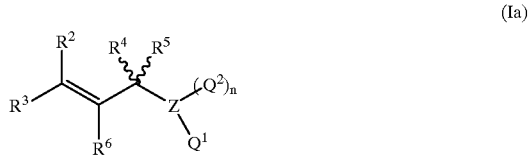
(Ia)

and the latter compounds have the structure (Ib)

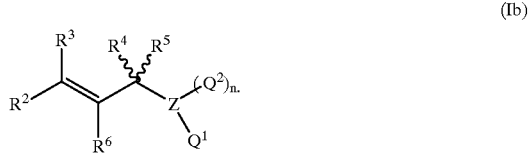
(Ib)

Reaction of compound (Ia) with the acid chloride (II)

(II)

will give rise to the product (IIIa)

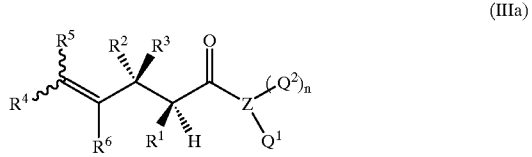
(IIIa)

while reaction of compound (Ib) with the acid chloride gives rise to the product (IIIb)

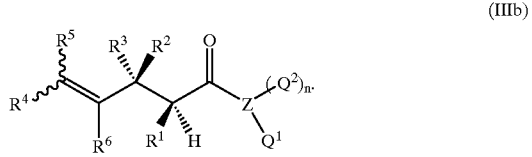
(IIIb)

Thus, a cis $R^2$ substituent results in an anti configuration in the product, while a trans $R^2$ substituent results in a syn configuration in the product.

Analogously, the size of the $R^4$ and $R^5$ substituents determines the relative position of $R^4$ and $R^5$ in the final product. A sterically bulky $R^4$ or $R^5$ substituent will result in the positioning of that substituent in the trans position in the product (i.e., trans to the carbon atom bound to $R^2$ and $R^3$), while a relatively smaller $R^4$ or $R^5$ substituent will result in the positioning of that substituent in the cis position in the product (i.e., cis to the carbon atom bound to $R^2$ and $R^3$. For example, an allylic reactant having the formula (Ic)

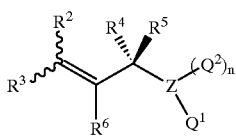

(Ic)

will give rise to the product (IIIc) when $R^4$ is a bulky substituent (e.g., phenyl) and $R^5$ is a relatively small substituent (e.g., hydrido)

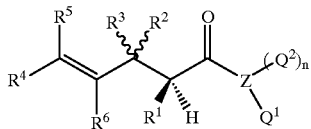

(IIIc)

but will result in the product (IIId)

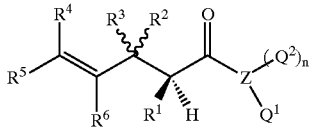

(IIId)

when $R^4$ is a relatively small substituent (e.g., hydrido) and $R^5$ is a bulky substituent (e.g., phenyl).

Procedurally, the reaction of the allylic reactant (I) with the acid chloride (II) is carried out as follows. The Lewis acid component (V) of the catalyst composition is combined with the allylic reactant (I) in a suitable solvent, e.g., an aliphatic hydrocarbon, an aromatic hydrocarbon, a halohydrocarbon, an ether, a cyclic ether, or the like. Suitable hydrocarbon solvents include isobutane, butane, pentane, hexane, octane, cyclohexane, methylcyclohexane, benzene, toluene, and the like. Preferred solvents are polar organic solvents, including halohydrocarbons, ethers, and the like, and particularly preferred solvents include such methylene chloride, tetrahydrofuran, diethylether, dimethylether, diisopropylether, dimethoxymethane, dioxane, acetone, methyl ethyl ketone, isobutyl methyl ketone, dimethylformamide, dimethylacetamide, N-methylpyrrolidone, acetonitrile and chloroform. Methylene chloride is most preferred. Solvents may be used alone or in combination.

The tertiary amine or non-nitrogenous base component of the catalyst composition is then added to the reaction mixture, followed by addition of the acid chloride (II). The reaction is continued until the allylic reactant is completely consumed as determined, for example, using thin layer chromatography. Generally, the reaction is complete within about 2 to 48 hours, typically within about 2 to 6 hours. After completion, the product is recovered using any suitable means known to those skilled in the art. The recovery process can include separation of by-products, if any, and evaporation of the solvent. The product may be recovered, for example, by extraction, recrystallization, filtration, or other purification processes known in the art.

The catalytic reaction is preferably although not necessarily homogeneous, and may be carried out in batch, semi-continuously or continuously, under inert, nonaqueous conditions (e.g., under an atmosphere of dry nitrogen and in an organic, completely nonaqueous solvent), at autogenous pressure or higher, depending, for example, on the nature of the catalyst composition and reactants used. The reaction temperature will generally be in the range of about −100° C. to 200° C., preferably in the range of about −78° C. to 100° C., most preferably in the range of about 0° C. to 50° C.; the reaction may be conveniently carried out at room temperature. The amount of total catalyst composition—i.e., the total of the Lewis acid component and the tertiary amine or non-nitrogenous base component—is generally in the range of 5 mole % to 300 mole % relative to the allylic reactant (I), the molar ratio of the Lewis acid component to the base component in the catalyst composition is generally in the range of about 1:2 to 2:1, preferably in the range of about 1.25:1 to 1:1.25, and the molar ratio of the reactants, i.e., the molar ratio of the allylic reactant (I) to the acid chloride (II), is typically in the range of about 1:10 to 10:1, preferably in the range of about 1:2 to 2:1, and most preferably is about 1:1.

The novel Claisen rearrangement reaction can also be carried out on a solid support, using solid phase synthesis techniques. Solid-phase synthesis enables use of the reaction in combinatorial chemistry processes, wherein an array or "matrix" of reactions is conducted in parallel on a single substrate. In this embodiment, the allylic reactant (I), the acid chloride (II), or the catalyst is bound either directly or indirectly to the surface of a solid substrate, if indirectly, through a cleavable or noncleavable linker. For example, the allylic reactant (I) can be linked to the surface of a substrate through $R^6$, $Q^1$, $Q^2$, or the like, and the acid chloride (II) can be linked to the surface of a substrate through the methylene group linking $R^1$ to the carbonyl moiety. Any solid support may be used. Typical substrates are those conventionally used in solid phase chemistry and which allow for chemical synthesis thereon. The only limitation upon the materials useful for constructing substrates is that they must be compatible with the reaction conditions to which they are exposed. Suitable substrates useful in practicing the methods of the invention include, but are not limited to, organic and inorganic polymers (e.g., polyethylene, polypropylene, polystyrene, polytetrafluoroethylene), metal oxides (e.g., silica, alumina), mixed metal oxides, metal halides (e.g., magnesium chloride), minerals, quartz, zeolites, and the like. Other substrate materials will be apparent to those of skill in the art.

The present invention thus represents an important contribution to the field of synthetic organic chemistry by providing an entirely new method for conducting Claisen rearrangement reactions using Lewis acid catalysis and an acid chloride as a reactant. The present process is useful in conjunction with an enormous variety of reactants and Lewis acid catalyst compositions, and, importantly, can be used as a "one-pot" synthesis to prepare chiral compounds in enantiomerically pure form.

It is to be understood that while the invention has been described in conjunction with the preferred specific embodiments thereof, that the description above as well as the examples which follow are intended to illustrate and not limit the scope of the invention. Other aspects, advantages and modifications within the scope of the invention will be apparent to those skilled in the art to which the invention pertains.

All patents, patent applications, journal articles and other reference cited herein are incorporated by reference in their entireties.

EXPERIMENTAL

In the following example, efforts have been made to ensure accuracy with respect to numbers used (e.g., amounts, temperature, etc.) but some experimental error and deviation should be accounted for. Unless indicated otherwise, temperature is in degrees C. and pressure is at or near atmospheric.

General Information: All non-aqueous reactions were performed using flame- or oven-dried glassware under an atmosphere of dry nitrogen. Commercial reagents were purified prior to use following the guidelines of Perrin and Armarego, *Purification of Laboratory Chemicals,* Fourth Edition (Oxford, Butterworth-Heinemann, 1996). Non-aqueous reagents were transferred under nitrogen via syringe or cannula. Organic solutions were concentrated under reduced pressure on a Büchi rotary evaporator. Tetrahydrofuran and diethyl ether were distilled from sodium benzophenone ketyl prior to use. N,N-diisopropylethylamine and dichloromethane were distilled from calcium hydride prior to use. Air sensitive solids were dispensed in an inert atmosphere glovebox. Chromatographic purification of products was accomplished using forced-flow chromatography on ICN 60 32-64 mesh silica gel 63 according to the method of Still et al. (1978) *J. Org. Chem.* 43:2923. Thin-layer chromatography (TLC) was performed on EM Reagents 0.25 mm silica gel 60-F plates. Visualization of the developed chromatogram was performed by fluorescence quenching or $KMnO_4$ stain.

$^1H$ and $^{13}C$ NMR spectra were recorded on Bruker DRX-500 (500 MHZ and 125 MHZ, respectively), AMX-400 (400 MHZ and 100 MHZ), or AMX-300 (300 MHZ and 75 MHZ) instruments, as noted, and are internally referenced to residual protio solvent signals. Data for $^1H$ are reported as follows: chemical shift (δ ppm), multiplicity (s=singlet, d=doublet, t=triplet, q=quartet, m=multiplet), integration, coupling constant (Hz) and assignment. Data for $^{13}C$ are reported in terms of chemical shift. IR spectra were recorded on an ASI React-IR 1000 spectrometer and are reported in terms of frequency of absorption ($cm^{-1}$). Mass spectra were obtained from the UC Berkeley Mass Spectral facility. Gas chromatography was performed on Hewlett-Packard 5890A and 6890 Series gas chromatographs equipped with a split-mode capillary injection system and flame ionization detectors using the following columns: Bodman Chiraldex Γ-TA (30 m×0.25 mm) and C&C Column Technologies CC-1701 (30 m×0.25 mm).

General Procedure A: A round-bottomed flask containing $TiCl_4 \cdot (THF)_2$ was charged with $CH_2Cl_2$, then treated with the allylic morpholine, followed by i-$Pr_2NEt$. The solution was stirred for 5 min before a solution of the acid chloride in $CH_2Cl_2$ was added dropwise over 1 min. The resulting dark red solution was stirred until the allylic morpholine was completely consumed (2–6 h) as determined by TLC (EtOAc). The reaction mixture was then diluted with an equal volume of $Et_2O$ and washed with aqueous 1N NaOH (5 mL). The aqueous layer was then extracted with ether, and the combined organic layers washed with brine, dried ($Na_2SO_4$), and concentrated. The resulting residue was purified by silica gel chromatography ($Et_2O$) to afford the title compounds.

General Procedure B: A round-bottomed flask containing $TiCl_4 \cdot (THF)_2$ was charged with $CH_2Cl_2$, then treated with the allylic morpholine, followed by i-$Pr_2NEt$. The solution was stirred for 5 min before a solution of the acid chloride in $CH_2Cl_2$ was added slowly by syringe pump over 4–10 h. The resulting dark red solution was stirred until the allylic morpholine was completely consumed (2–6 h) as determined by TLC (EtOAc). The reaction mixture was then diluted with an equal volume of $Et_2O$ and washed with aqueous 1$N$ NaOH (5 mL). The aqueous layer was then extracted with ether, and the combined organic layers washed with brine, dried ($Na_2SO_4$), and concentrated. The resulting residue was purified by silica gel chromatography ($Et_2O$) to afford the title compounds.

The proposed mechanism for these reactions is illustrated in FIG. 1. As outlined in the figure, the acid chloride is believed to be converted by the tertiary amine component ($NR_3$) of the catalyst composition to ketene 1. The ketene is activated toward the addition of tertiary allylic amine 2 by the Lewis acid (LA) component of the catalyst composition. The intermediate formed by addition of the ketene to the tertiary allylic amine gives rise to the intermediate zwitterionic allyl-vinylammonium complex 3, which then undergoes [3,3]-bond reorganization to provide Claisen adduct 4. Release of the Lewis acid from adduct 4 results in the desired product.

Example 1

Preparation of (2R*,3S*)-'(2,3-Dimethyl-4-pentenoyl)-morpholine (5)

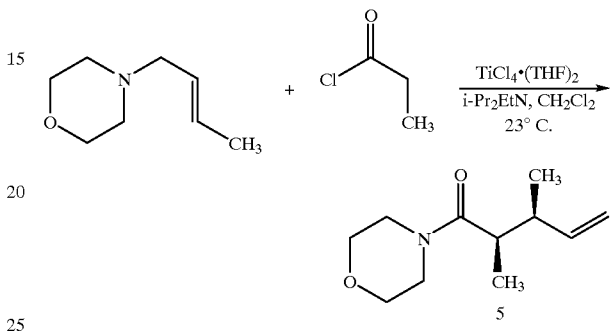

Prepared according to general procedure A from (E)-N-but-2-enyl morpholine (115 mg, 0.81 mmol), $TiCl_4 \cdot (THF)_2$ (27 mg, 81 μmol), i-$Pr_2NEt$ (213 μL, 1.22 mmol), and propionyl chloride (980 μL, 1 M solution in $CH_2Cl_2$, 0.98 mmol) in $CH_2Cl_2$ (8.1 mL) to provide the pure product as a colorless oil in 92% yield (148 mg, 0.75 mmol); >99:1 syn:anti. Syn isomer: IR ($CH_2Cl_2$) 2972, 2926, 2860, 1633, 1459, 1436 $cm^{-1}$; $^1H$ NMR (300 MHZ, $CDCl_3$) δ5.68 (ddd, J=7.3, 10.4, 17.5 Hz, 1H, CH=$CH_2$), 4.87–4.96 (m, 2H, CH=$CH_2$), 3.34–3.60 (m, 8H, N($CH_2CH_2$)$_2$), 2.52 (dq, J=7.1, 7.1 Hz, 1H, CHCH$_3$), 2.37 (q, J=7.1 Hz, 1H, CHCH$_3$), 1.01 (d, J=6.7 Hz, 3H, $CH_3$), 0.94 (d, J=6.8 Hz, 3H, $CH_3$); $^{13}C$ NMR (75 MHZ, $CDCl_3$) δ174.7, 142.3, 114.3, 67.3, 67.0, 46.5, 42.3, 40.5, 40.3, 16.3, 14.8; LRMS (FAB) m/z 197(M)$^+$; HRMS (FAB) exact mass calcd for ($C_{11}H_{19}NO_2$) requires m/z 197.1416, found m/z 197.1414. Product ratio was determined by GLC with a Bodman Γ-TA column (70° C., 2° C./min gradient, 23 psi); syn adduct (2R,3S and 2S,3R) $t_r$=39.7 min and 40.8 min, anti adduct (2R,3R and 2S,3S) $t_r$=39.9 min and 40.5 min.

Determination of the Relative Configuration of (2R*,3S*)-'(2,3-Dimethyl4-pentenoyl)-morpholine (3) by Correlation with (2R*,3S*)-2,3-Dimethyl-4-pentenoic acid: The relative configuration of (3) was determined by correlation with (2R*,3S*)-2,3-dimethyl-4-pentenoic acid according to the following scheme:

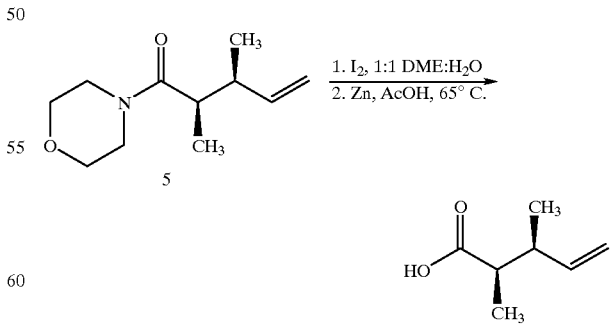

A solution of (2R*,3S*)-'(2,3-dimethyl-4-pentenoyl)-morpholine 5 (22 mg, 0.11 mmol) in 1,2-DME (0.25 mL) and $H_2O$ (0.25 mL) was placed in an 8 mL scintillation vial equipped with a magnetic stir bar. The solution was treated with iodine (61 mg, 0.24 mmol) and was stirred in the absence of light. After 30 min, the reaction was diluted with Et$_2$O (1 mL) and washed sequentially with 10% aqueous Na$_2$S$_2$O$_3$ (1 mL) and brine (1 mL). The resulting organic layer was dried (Na$_2$SO$_4$) and concentrated to give (2S*, 3S*,4R*)-4-iodomethyl-2,3-dimethyl-γ-butyrolactone as a yellow oil. This crude residue was dissolved in glacial AcOH (1 mL) and placed in an 8 mL scintillation vial equipped with a magnetic stir bar. The solution was treated with zinc dust (65 mg, 1.0 mmol) and stirred at 65° C. for 3 h. After allowing the reaction to cool to rt, 1 N HCl (aq) (1 mL) was added, and the mixture was extracted with ether (3×1 mL). The organic extracts were combined, dried (Na$_2$SO$_4$), and concentrated to give a light pink oil that exhibited spectral data identical in all respects to those reported for (2R*,3S*)-2,3-dimethyl-4-pentenoic acid (Metz (1993) *Tetrahedron* 49:6367).

Example 2

Preparation of (2S*,3*)-'(2-Methyl-3-phenyl-4-pentenoyl)-morpholine (6)

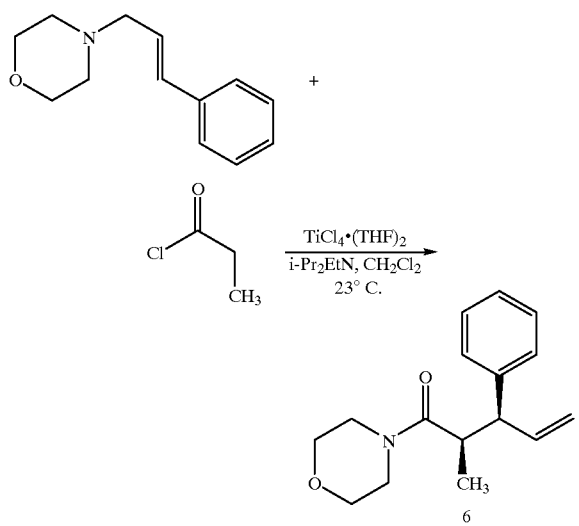

Prepared according to general procedure A from (E)-'(3-phenyl-2-propenyl)-morpholine (201 mg, 0.99 mmol), TiCl$_4$.(THF)$_2$ (33 mg, 99 μmol), i-Pr$_2$NEt (258 μL, 1.43 mmol), and propionyl chloride (1.48 mL, 1 M solution in CH$_2$Cl$_2$, 1.48 mmol) in CH$_2$Cl$_2$ (10 mL) at 0° C. to provide the pure product as white needles in 74% yield (194 mg, 0.75 mmol); >99:1 syn:anti. Syn isomer: IR (CH$_2$Cl) 3057, 2988, 2968, 2930, 1637, 1436 cm$^{-1}$; $^1$H NMR (400 MHZ, CDCl$_3$) δ7.15–7.31 (m, 5H, Ph), 5.99 (ddd, J=7.8, 10.4, 17.9 Hz, 1H, CH=CH$_2$), 4.95–5.02 (m, 2H, CH=CH$_2$), 3.48–3.66 (m, 9H, N(CH$_2$CH$_2$)$_2$, CHPh), 3.04 (dq, J=6.8, 9.9 Hz, 1H, CHCH$_3$), 0.90 (d, 3H, CH$_3$); $^{13}$C NMR (100 MHZ, CDCl$_3$) δ174.0, 141.7, 139.8, 128.6, 128.3, 126.7, 115.7, 67.0, 66.7, 53.4,46.2,42.1, 39.7, 16.7; LRMS (FAB) m/z 259; HRMS (FAB) exact mass calcd for (C$_{16}$H$_{21}$NO$_2$) requires m/z 259.1572, found m/z 259.1569. Diastereomer ratio was determined by GLC with a CC-1701 column (70° C., 5° C./min gradient, 25 psi); syn adduct t$_r$=31.3 min, anti adduct t$_r$=30.2 min.

Example 3

Preparation of (2R*,3S*)-N-(3-Chloro-2-methyl-4-pentenoyl)-morpholine (7)

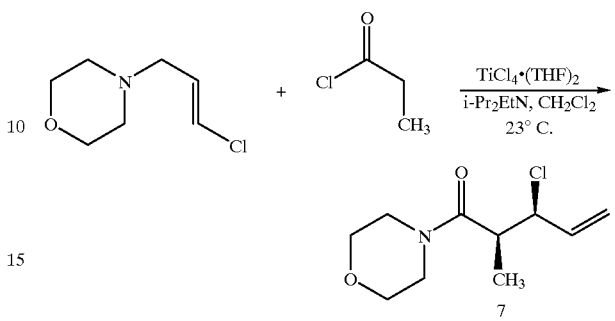

Prepared according to general procedure A from (E)-N-(3-chloro-2-propenyl)morpholine (112 mg, 0.69 mmol), TiCl$_4$.(THF)$_2$ (23 mg, 69 μmol), i-Pr$_2$NEt (181 μL, 1.04 mmol), and propionyl chloride (1.04 mL, 1 M solution in CH$_2$Cl$_2$, 1.04 mmol) in CH$_2$Cl$_2$ (7 mL) to provide the pure product as a pale yellow oil in 95% yield (143 mg, 0.66 mmol); >99:1 syn:anti. Syn isomer: IR (CH$_2$Cl$_2$) 3057, 2976, 2864, 1640, 1463, 1440 cm$^{-1}$; $^1$H NMR (300 MHZ, CDCl$_3$) δ5.87 (ddd, J=8.3, 10.2, 18.5 Hz, 1H, CH=CH$_2$), 5.12–5.31 (m, 2H, CH=CH$_2$), 4.51 (t, J=8.4 Hz, 1H, CHCl), 3.50–3.65 (m, 8H, N(CH$_2$CH$_2$)$_2$), 2.98 (dq, J=6.8, 8.8 Hz, 1H, CHCH$_3$), 1.27 (d, J=6.8, 3H, CH$_3$); $^{13}$C NMR (75 MHZ) δ172.0, 136.6, 118.4, 67.2, 67.0, 65.4, 46.7, 42.7, 42.5, 16.7; LRMS (FAB) m/z 217 (M)$^+$; HRMS (FAB) exact mass calcd for (C$_{10}$H$_{16}$ClNO$_2$) requires m/z 217.0870, found m/z 217.0868. Product ratio was determined by GLC with a Bodman Γ-TA column (70° C., 7° C./min gradient, 23 psi); syn adduct (2R,3S and 2S,3R) t$_r$=18.7 min and 19.2 min, anti adduct (2R,3R and 2S,3S) t$_r$=19.6 min and 19.8 min. Relative configuration assigned by analogy.

Example 4

Preparation of N-(2-Methyl-4-pentenoyl)morpholine (8)

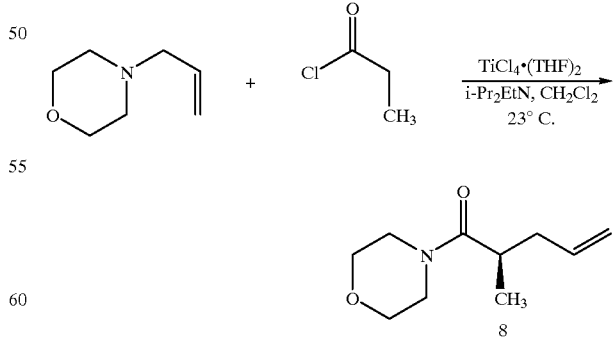

Prepared according to general procedure A from N-allyl morpholine (161 mg, 1.3 mmol), TiCl$_4$.(THF)$_2$ (42 mg, 0.13 mmol), i-Pr$_2$NEt (336 μL, 0.94 mmol), and propionyl chloride (1.5 mL, 1 M solution in CH$_2$Cl$_2$, 1.5 mmol) in CH$_2$Cl$_2$(13 mL) to provide the pure product as a clear oil in 95% yield (221 mg, 1.2 mmol); IR (CH$_2$Cl$_2$) 2976, 2864, 1640, 1467, 1436 cm$^{-1}$; $^1$H NMR (400 MHZ) δ5.66–5.77 (m, 1H, CH=CH$_2$), 4.96–5.05 (m, 2H, CH=CH$_2$), 3.47–3.64 (m, 8H, N(CH$_2$CH$_2$)$_2$), 2.64–2.72 (m, 1H, CHCH$_3$), 2.35–2.42 (m, 1H, CH$_2$CH=CH$_2$), 2.06–2.13 (m, 1H, CH$_2$CH=CH$_2$), 1.08 (d, 3H, CH$_3$); $^{13}$C NMR (100 MHZ) δ174.5, 136.0, 116.7, 67.0, 66.8, 46.0, 42.1, 38.1, 35.1, 17.3; LRMS (FAB) m/z 183 (M)$^+$; HRMS (FAB) exact mass calcd for (C$_{10}$H$_{17}$NO$_2$) requires m/z 183.1259, found m/z 183.1253.

Example 5

Preparation of (2R*,3R*)-N-(2,3-Dimethyl-4-pentenoyl)-morpholine (9)

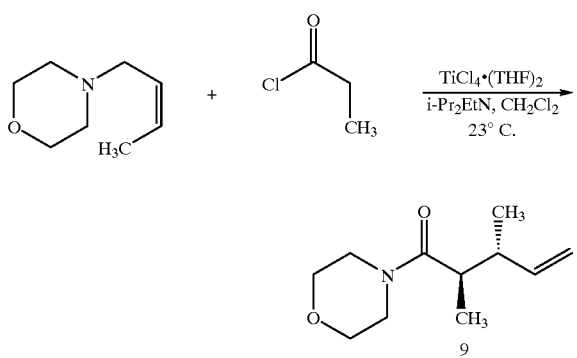

Prepared according to general procedure B from (Z)-N-but-2-enyl morpholine (88 mg, 0.62 mmol), TiCl$_4$·(THF)$_2$ (42 mg, 0.13 mmol), i-Pr$_2$NEt (163 μL, 0.94 mmol), and propionyl chloride (750 μL, 1 M solution in CH$_2$Cl$_2$, 0.75 mmol), added over 8h, in CH$_2$Cl$_2$ (4.2 mL) to provide the pure product as a clear oil in 74% yield (91 mg, 0.46 mmol); 95:5 anti:syn. Anti isomer: IR (CH$_2$Cl$_2$) 2976, 2864, 1637, 1463, 1436 cm$^{-1}$; $^1$H NMR (400 MHZ, CDCl$_3$) δ5.61 (ddd, J=8.2, 10.2, 18.3 Hz, 1H, CH=CH), 4.96–5.12 (m, 2H, CH=CH$_2$), 3.44–3.66 (m, 8H, N(CH$_2$CH$_2$)$_2$), 2.36–2.49 (m, 2H, CHCH3), 1.02 (d, J=6.5 Hz, 3H, CH$_3$), 0.94 (d, J=6.3 Hz, 3H, CH$_3$); $^{13}$C NMR (100 MHZ, CDCl$_3$) δ174.9, 141.6. 115.4, 67.4, 67.1, 46.5, 42.4, 41.8, 40.4, 19.3; LRMS (FAB) m/z 197 (M)$^+$; HRMS (FAB) exact mass for (C$_{11}$H$_{19}$NO$_2$) requires m/z 197.1416, found 197.1414. Product ratio was determined by GLC with a Bodman Γ-TA column (70° C., 2° C./min gradient, 23 psi); syn adduct (2R,3S and 2S,3R) t$_r$=39.7 min and 40.8 min, anti adduct (2R,3R and 2S,3S) t$_r$=39.9 min and 40.5 min.

The reactions and results of Examples 1–5 are set forth in Table 1. Table 1 illustrates that the Claisen reaction of the invention allows for substantial structural variation in the allyl substituent (H, alkyl, aryl or halogen, entries 1–4) without loss in yield or diastereoselectivity (>76% yield, >99:1 syn/anti). It may also be seen that complementary stereocontrol can be achieved through the appropriate selection of double bond geometry on the allyl component. While excellent levels of syn stereoselection are observed with trans-allylic morpholines (entries 1–3), the anti Claisen adduct is readily furnished (95:5 anti:syn) using the cis double bond isomer (entry 5).

TABLE 1

| entry | amine | mol % cat | product[a] | yield | syn:anti |
|---|---|---|---|---|---|
| 1 | (cis-morpholine-CH$_2$CH=CHMe) | 5 | (product 5, R=Me) | 92 | >99:1 |
| 2 | (cis-morpholine-CH$_2$CH=CHPh) | 10 | (product 6, R=Ph) | 76 | >99:1 |

TABLE 1-continued

| entry | amine | mol % cat | product[a] | yield | syn:anti |
|---|---|---|---|---|---|
| 3 | | 10 | | 95 | >99:1 |
| 4 | | 10 | | 95 | — |
| 5 | | 20 | | 74 | 5:95 |

[a]$NR_2$ = N-morpholine.

Example 6

Preparation of (2R*,3S*)-N-(Methyl-2-phthalimido-4-pentenoyl)-morpholine (10)

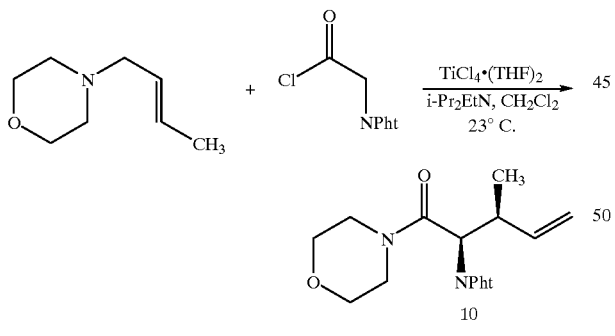

Prepared according to general procedure B from (E)-N-but-2-enyl morpholine (75 mg, 0.53 mmol), $TiCl_4 \cdot (THF)_2$ (17.7 mg, 53 μmol), i-$Pr_2$NEt (139 μL, 0.80 mmol), and phthalylglycyl chloride (1.3 mL, 0.5 M solution in $CH_2Cl_2$, 0.64 mmol), added over 3h, in $CH_2Cl_2$ (10.6 mL) to provide the pure product as white crystals in 77% yield (134 mg, 0.41 mmol); 98:2 syn:anti. Syn isomer: IR ($CH_2Cl_2$) 3065, 2976, 2864, 1776, 1718, 1660, 1459, 1436, 1382, 1359 $cm^{-1}$; $^1$H NMR (400 MHZ, $CDCl_3$) δ7.69–7.81 (m, 4H, PhH), 5.79 (ddd, J=7.6, 10.4, 17.5 Hz, 1H, CH=$CH_2$), 5.04–5.18 (m, 2H, CH=$CH_2$), 4.76 (d, J=10.2 Hz, 1H, CHN$R_2$), 3.63–3.71 (m, 1H, CHC$H_3$), 3.39–3.56 (m, 8H, N($CH_2CH_2$)$_2$), 0.95 (d, J=6.8 Hz, 3H, $CH_3$); $^{13}$C NMR (100 MHZ, $CDCl_3$) δ167.8, 166.5, 139.6, 134.4, 131.3, 123.6, 116.6, 66.8, 66.5, 54.5, 46.3, 42.5, 36.5, 16.5; LRMS (FAB) m/z 329 (MH)$^+$; HRMS (FAB) exact mass calcd for ($C_{18}H_{21}N_2O_4$)$^+$ requires m/z 329.1501, found m/z 329.1504. Diastereomer ratio was determined by GLC with a CC-1701 column (50° C., 5° C./min gradient, 25 psi); syn adduct $t_r$=51.8 min, anti adduct $t_r$=49.2 min.

Example 7

Preparation of (2R*,3S*)-N-(3-Methyl-2-phenylthio-4-pentenoyl)-morpholine (11)

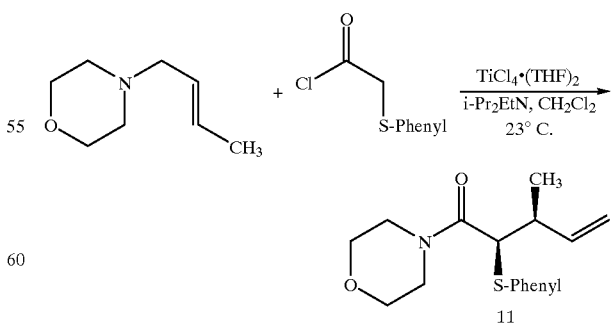

Prepared according to general procedure B from (E)-N-but-2-enyl morpholine (67 mg, 0.48 mmol), $TiCl_4 \cdot (THF)_2$ (15.9 mg, 47.5 μmol), i-$Pr_2$NEt (124 μL, 0.71 mmol), and phenylthioacetyl chloride (569 μL, 1 M solution in CH₂Cl₂, 0.57 mmol), added over 4 h, in CH₂Cl₂ (9.5 mL) to provide the pure product as a light orange oil in 81% yield (107 mg, 0.39 mmol); syn:anti 92:8. Syn isomer: IR (CH₂Cl₂) 3053, 2976, 2864, 1640, 1436 cm⁻¹; ¹H NMR (400 MHZ, CDCl₃) δ7.47–7.49 (m, 2H, Ph), 7.28–7.30 (m, 3H, Ph), 5.75 (ddd, J=7.5, 8.8, 16.3 Hz, 1H, CH=CH₂), 4.99–5.10 (m, 2H, CH=CH₂), 3.73 (d, J=9.7 Hz, 1H, CHSPh), 3.11–3.58 (m, 8H, N(CH₂CH₂)₂), 2.76–2.82 (m, 1H, CHCH₃), 1.28 (d, J=6.8 Hz, 3H, CH₃); ¹³C NMR (100 MHZ, CDCl₃) δ169.7, 140.3, 134.0, 129.1, 128.4, 115.6, 78.3, 66.9, 66.4, 53.9, 46.4, 42.3, 39.7, 17.9; LRMS (FAB) m/z 292 (MH)⁺; HRMS (FAB) exact mass calcd for (C₁₆H₂₂NO₂S) requires m/z 292.1371, found m/z 292.1373. Diastereomer ratios were determined by ¹H NMR analysis. Relative configuration assigned by analogy.

Example 8

Preparation of (2R*,3S*)-N-(2-Benzyloxy-3-methyl-4-pentenoyl)-morpholine (12)

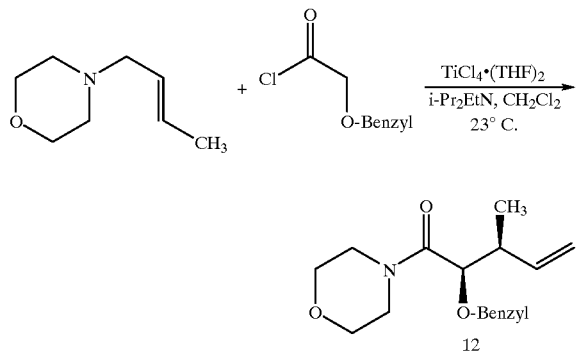

Prepared according to general procedure B from (E)-N-(3-phenyl-2-propenyl)-morpholine (60 mg, 0.43 mmol), TiCl₄·(THF)₂ (14 mg, 43 μmol), i-Pr₂NEt (111 μL, 0.64 mmol), and benzyloxyacetyl chloride (0.51 mL, 1 M solution in CH₂Cl₂, 0.51 mmol), added over 2 h, in CH₂Cl₂ (8.5 mL) to provide the pure product as a pale yellow oil in 91% yield (112 mg, 0.39 mmol); 86:15 syn:anti. Syn isomer: IR (CH₂Cl₂) 3068, 2746, 2864, 1640, 1455 cm⁻¹; ¹H NMR (400 MHZ, CDCl₃) δ7.27–7.36 (m, 5H, Ph), 5.68 (ddd, J=8.3, 10.2, 18.5 Hz, 1H, CH=CH₂), 5.00–5.08 (m, 2H, CH=CH₂), 4.62 (d, J=11.7, 1H, CH₂Ph), 4.43 (d, J=11.7, 1H, CH₂Ph), 3.92 (d, J=8.9, 1H, CHOCH₂Ph), 3.55–3.70 (m, 8H, N(CH₂CH₂)₂), 2.55–2.62 (m, 1H, CHCH₃), 1.15 (d, J=6.6 Hz, 3H, CH₃); ¹³C NMR (100 MHZ, CDCl₃) δ169.5, 138.9, 137.3, 128.5, 128.0, 115.8, 84.2, 72.2, 67.1, 66.8, 45.7, 42.5, 41.5, 17.0; LRMS (FAB) m/z 290 (MH)⁺; HRMS (FAB) exact mass calcd for (C₁₇H₂₄NO₃) requires m/z 289.1756, found m/z 290.1755. Diastereomer ratios were determined by ¹H NMR analysis. Relative configuration assigned by analogy.

Example 9

Preparation of (2R*,3S*)-N-(2-Benzyloxy-3-chloro4-pentenoyl)-morpholine (13)

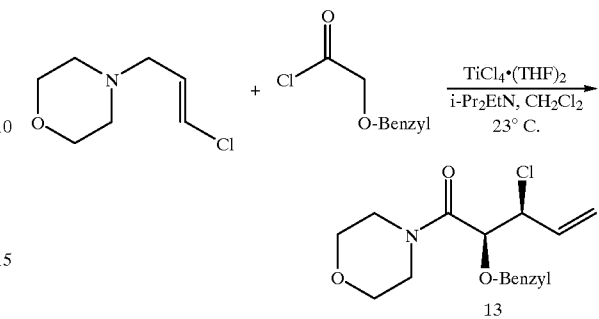

Prepared according to the general procedure A from (E)-N-(3-chloro-2-propenyl)-morpholine (100 mg, 0.62 mmol), TiCl₄·(THF)₂, (21 mg, 62 μmol), i-Pr₂NEt (151 μL, 86.7 mmol), and propionyl chloride (0.74 mL, 1 M solution in CH₂Cl₂, 0.74 mmol) in CH₂Cl₂ (12 mL) to provide the pure product as a yellow oil in 84% yield (160 mg, 0.52 mmol); 90:10 syn:anti. Syn isomer: IR (CH₂Cl₂) 3053, 2976, 2907, 2864, 1648, 1444, 1274, 1247, 1116 cm⁻¹; ¹H NMR (400 MHZ) δ7.30–7.40 (m, 5H, Ph), 5.92 (ddd, J=8.5 Hz, J=10.1 Hz, J=16.9 Hz, 1H, CH=CH₂) 5.39 (d, J=16.9 Hz, 1H, CH=CH₂), 5.26 (d, J=10.2 Hz, 1H; CH=CH₂), 4.72–4.73 (m, 1H, CHCl), 4.71 (d, J=11.7 Hz, 1H, CH₂Ph), 4.57 (d, J=11.7 Hz, 1H, CH₂Ph), 4.33 (d, J=7.4 Hz, 1H, CHOCH₂Ph), 3.50–3.65 (m, 8H, N(CH₂CH₂)₂); ¹³C NMR (100 MHZ) δ167.0, 136.5, 134.4, 128.5, 128.3, 128.1, 119.5, 82.4, 72.5, 66.9, 66.7, 62.4, 45.8, 42.8; LRMS (FAB) m/z 310 (MH)⁺; HRMS (FAB) exact mass calcd for (C₁₆H₂₁ClNO₃)⁺ requires m/z 310.1210, found m/z 310.1213. Diastereomer ratio was determined by GLC with a CC-1701 column (80° C., 20° C./min gradient for 1 min, then 10° C./min, 23 psi); syn adduct t_r=19.2 min, anti adduct t_r=19.3 min.

Example 10

Preparation of (2R*,3R*)-N-(2-Benzyloxy-3-chloro4-pentenoyl)-morpholine (14)

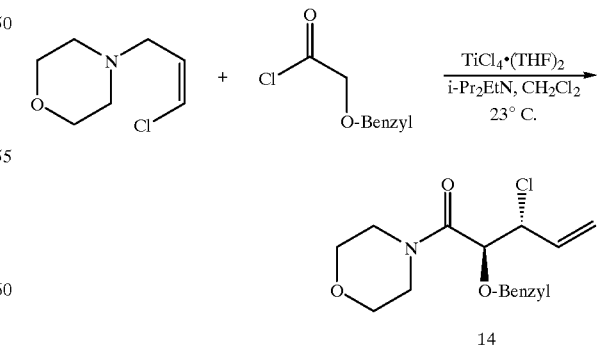

Prepared according to the general procedure A from (Z)-N-(3-chloro-2-propenyl)-morpholine (82 mg, 0.51 mmol), TiCl₄·(THF)₂, (17 mg, 51 μmol), i-Pr₂NEt (290 μL, 1.66 mmol), and propionyl chloride (1.52 mL, 1 M solution in $CH_2Cl_2$, 1.52 mmol) in $CH_2Cl_2$ (10 mL) to provide the pure product as a yellow oil in 71% yield (110 mg, 0.36 mmol); 90:10 anti:syn. Anti isomer: IR ($CH_2Cl_2$) 3057, 2976, 2907, 1652, 1444, 1239, cm$^{-1}$; $^1$H NMR (400 MHZ) δ7.29–7.38 (m, 5H, Ph), 6.00 (ddd, J=8.4 Hz, J=10.1 Hz, J=16.9 Hz, 1H, CH=CH$_2$), 5.48 (dd J=0.9 Hz, J=16.0 Hz, 1H, CH=CH$_2$), 5.35 (d, J=10.2 Hz, 1H, CH=CH$_2$), 4.75 (t, J=8.3 Hz, 1H, CHCl), 4.63 (d, J=12.0 Hz, 1H, CH$_2$Ph), 4.51 (d, J=12.0 Hz, 1H, CH$_2$Ph), 4.33 (d, J=8.3 Hz, 1H, CHOCH$_2$Ph), 3.50–3.70 (m, 8H, N(CH$_2$CH$_2$)$_2$); $^{13}$C NMR (100 MHZ) δ167.3, 136.7, 134.5, 128.6, 128.3, 128.1, 119.8, 78.5, 71.9, 66.9, 66.6, 60.5, 46.0, 42.7; LRMS (FAB) m/z 310 (MH)$^+$; HRMS (FAB) exact mass calcd for (C$_{16}$H$_{21}$ClNO$_3$)$^+$ requires m/z 310.1210, found m/z 310.1213. Diastereomer ratio was determined by GLC with a CC-1701 column (80° C., 20° C./min gradient for 1 min, then 10° C./min, 23 psi); syn adduct t$_r$=19.2 min, anti adduct t$_r$=19.3 min.

The reactions and results of Examples 6–10 are set forth in Table 2. Table 2 illustrates that the Claisen reaction of the invention is quite general with respect to the acid chloride structure.

TABLE 2

| entry | amine[a] | acid-Cl | product[a] | yield | syn:anti |
|---|---|---|---|---|---|
| 1 | R$_2$N-CH=CH-Me | Cl-C(O)-CH$_2$-NPht | R$_2$N-C(O)-CH(NPht)-CH(Me)-CH=CH$_2$ 10 | 77 | >99:1 |
| 2 | R$_2$N-CH=CH-Me | Cl-C(O)-CH$_2$-SPh | R$_2$N-C(O)-CH(SPh)-CH(Me)-CH=CH$_2$ 11 | 81 | 92:8 |
| 3 | R$_2$N-CH=CH-Me | Cl-C(O)-CH$_2$-OBn | R$_2$N-C(O)-CH(OBn)-CH(Me)-CH=CH$_2$ 12 | 91 | 86:14 |
| 4 | R$_2$N-CH=CH-Cl | Cl-C(O)-CH$_2$-OBn | R$_2$N-C(O)-CH(OBn)-CH(Cl)-CH=CH$_2$ 13 | 83 | 90:10 |
| 5 | R$_2$N-CH=CH-Cl (Z) | Cl-C(O)-CH$_2$-OBn | R$_2$N-C(O)-CH(OBn)-CH(Cl)-CH=CH$_2$ 14 | 70 | 10:90 |

[a]NR$_2$ = N-morpholine.

As shown in entry 1, the methodology provides a new strategy for the catalytic production of unnatural β-substituted α-amino acids using α-phthalylglycyl chloride (77% yield, 98:2 syn:anti). The process is also tolerant of oxygen and sulfur substituents on the acyl chloride component (>81% yield, 86:14 to 92:8 syn/anti, entries 2–3). An important feature of the new Claisen process is the capacity to build diverse functional and stereochemical arrays that are not readily available using conventional catalytic methods. For example, both the syn and anti α-oxy, β-chloro Claisen isomers 13 and 14 can be obtained in high yield and stereospecificity from chloro-substituted allyl morpholines and α-benzyloxyacetyl chloride (entries 4–5).

Example 11

The procedure of Example 1 was repeated four times, with (1) no Lewis acid, (2) Yb(OTf)$_3$ (OTf=triflate) in place of TiCl$_4$.THF$_2$, (3) AlCl$_3$ in place of TiCl$_4$.THF$_2$, and (4) Ti(O—Pr)$_2$Cl$_2$ in place of TiCl$_4$.THF$_2$. The results are set forth in Table 3; as may seen therein, each Lewis acid resulted in a syn:anti ratio of greater than 99:1.

TABLE 3

| entry | Lewis acid | mol % cat | % yield | syn:anti |
|---|---|---|---|---|
| 1 | — | — | NR | — |
| 2 | Yb(OTf)$_3$ | 10 | 80 | >99:1 |
| 3 | AlCl$_3$ | 10 | 90 | >99:1 |
| 4 | Ti(Oi-Pr)$_2$Cl$_2$ | 10 | 76 | >99:1 |
| 5 | TiCl$_4$.THF$_2$ | 5 | 92 | >99:1 |

Example 12

Rearrangement of 3-Methyl-1-Morpholinocyclohexene (15) to (1'S*,2R)-N-(2-(1'-Methylcyclohex-2'-enyl)-propanoyl)-morpholine (16)

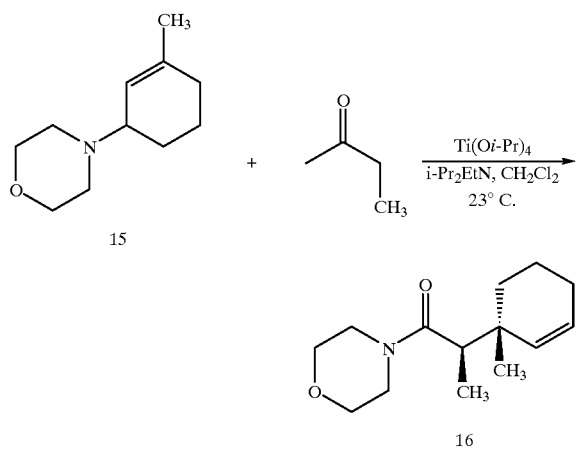

(a) Preparation of 3-Methyl-1-morpholinocyclohexene (15): To a solution of 3-methyl-2-cyclohexen-1-one (1.50 g, 13.7 mmol) and morpholine (3.57 g, 41.0 mmol) in CH$_2$Cl$_2$ (120 mL) was added Ti(Oi-Pr)$_4$. The reaction was monitored by IR for disappearance of the ketone. After 6 h the solution was concentrated and EtOH (45 mL) was added followed by Na(CN)BH$_3$ (1.81 g, 28.8 mmol). The solution was stirred for 1 h before 1N NaOH (30 mL) was added. The resulting mixture was extracted with EtOAc (3×50 mL), and the combined organic extracts were dried over Na$_2$SO$_4$ and concentrated to give an orange oil. The residue was purified by column chromatography on silica gel using EtOAc to furnish the product as a brown oil in 19% yield (0.47 g). The spectral data for 15 were in complete agreement with previously reported literature values (Birch et al. (1971) *J. Chem. Soc. Comm,* p. 2409).

(b) Preparation of (1'S*,2R)-N-(2-(1'-Methylcyclohex-2'-enyl)-propanoyl)-morpholine (16). Prepared according to general procedure A from 15 (50 mg, 0.28), TiCl$_4$.(THF)$_2$, (9 mg, 27 μmol), i-Pr$_2$NEt (71 μL, 0.41 mmol), and propionyl chloride (0.41 mL, 1M solution in CH$_2$Cl$_2$, 0.41 mmol) in CH$_2$Cl$_2$ (3 mL) to provide the product as a yellow oil in 72% yield (45 mg, 0.36 mmol); 95:5 dr. Major isomer: IR (CH$_2$Cl$_2$) 2968, 2934, 2864, 1633, 1459, 1432, 1239, 1116 cm$^{-1}$; $^1$H NMR (400 MHZ) δ5.72 (d, J=10.2 Hz, 1H, CH$_2$CH=CH), 5.64 (m, 1H, CH$_2$CH=CH), 3.54–3.70 (m, 8H, N(CH$_2$CH$_2$)$_2$), 2.62 (q, J=6.9 Hz, 1H CHC=O), 1.92 (m, 2H, CH$_2$CH=CH), 1.68–1.73 (m, 1H, CH$_2$), 1.53–1.67 (m, 2H, CH$_2$), 1.34–1.39 (m, 1H, CH$_2$), 1.09 (d, J=6.9 Hz, 3H, CH$_3$CHC=O), 1.06 (s, 3H, CH$_3$CCH=CH); $^{13}$C NMR (100 MHZ) δ174.5, 134.1, 126.4, 67.1, 66.8, 50.1, 46.9, 42.1, 37.4, 33.2, 25.0, 24.7, 19.2, 13.3; LRMS (FAB) m/z 237 (M)$^+$; HRMS (FAB) exact mass calcd for (C$_{14}$H$_{23}$NO$_2$) requires m/z 237.1729, found m/z 237.1731. Diastereomer ratios were determined by $^1$H NMR analysis.

Example 13

Rearrangement of (E)-N-(3-Ethyl-3-methyl-2-propenyl)-morpholine (17) to (2R*,3R*)-N-(2,3-Dimethyl-3-ethyl-4-pentenoyl)-morpholine (18)

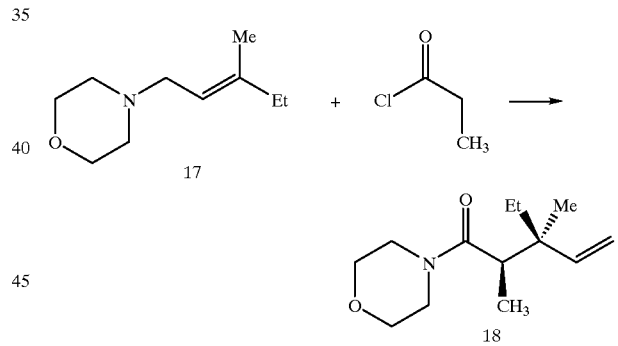

(a) Preparation of (E)-N-(3-Ethyl-3-methyl-2-propenyl)-morpholine (17): 2-Methyl-3-penten-1-ol was prepared using a modification of the procedure outlined by Corey and coworkers (Corey et al. (1973)*Tetrahedron Lett.* 18:1611). To a solution of 2-pentyn-1-ol (2.5 mL, 27 mmol) in THF (100 mL) was added Red-Al (8.1 mL of a 3.5 M solution in toluene, 28 mmol). The resulting solution was warmed to reflux for 3.5 h and then cooled to −78° C., before a solution of iodine (20.5 g, 81.0 mmol) in THF (50 mL) was added dropwise by syringe. The resulting solution was then allowed to warn to rt before Et$_2$O (200 mL) was added, and the reaction mixture washed with 5% Na$_2$SO$_4$ (3×200 mL), dried (Na$_2$SO$_4$), and concentrated to afford 3-iodo-2-penten-1-ol as a crude product that was used without further purification. To a solution of copper(I)iodide (20.1 g, 0.11 mol) and methyl lithium (162 mL of a 1.3 M solution in Et$_2$O, 0.21 mol) in Et$_2$O (60 mL) at 0° C. was added a solution of the crude 3-iodo-2-penten-1-ol. The reaction mixture was stirred at 0° C. for 62 h and then washed with sat. aq. NH$_4$Cl (3×200 mL), dried (Na$_2$SO$_4$), and concentrated to provide 2-methyl-3-penten-1-ol in 91% yield (2.1 g, 21 mmol) as a pure oil by $^1$H NMR analysis. Spectroscopic data of this material were in complete agreement with reported literature values. Normant et al. (1973) *Tetrahedron Lett.* 26:2407.

Morpholine 17 was prepared using a modification of the procedure outlined by Froyen and coworkers (Froyen et al. (1995) *Tetrahedron Lett.* 36:9555). To a solution of 2-methyl-3-penten-1-ol (1.3 g, 13 mmol) and triphenylphosphine (3.6 g, 14 mmol) in THF (10 mL) was added N-bromosuccinimide (2.5 g, 14 mmol). After 15 min, morpholine (2.7 mL, 31 mmol) was added dropwise and the resulting brown solution was heated to 70° C. for 2.5 h. Upon cooling to rt, the reaction mixture was diluted with Et$_2$O (25 mL) and filtered through a pad of Celite©. The filtrate was then extracted with aqueous 1N HCl (100 mL). The product containing aqueous layer was then washed with Et$_2$O (3×100 mL), and then made alkaline by the addition of NaOH (4 g). The aqueous solution was then extracted with Et$_2$O (3×100 mL), the combined organic layers dried (Na$_2$SO$_4$), and then concentrated by rotary evaporation at 0° C. under reduced pressure. The resulting residue was then distilled (110° C., 20 mm) to afford (E)-N-(3-ethyl-3-methyl-2-propenyl)-morpholine (16) as a colorless oil in 49% yield (1.0 g, 6.0 mmol); IR 2968, 1455, 1293, 1116, 1004, 907 cm$^{-1}$; $^1$H NMR(400 MHZ) δ5.21–5.25 (m, 1H, CH=CCH$_3$), 3.65–3.77 (m, 4H, O(CH$_2$)$_2$), 2.96 (d, J=7.0 Hz, 2H, CH$_2$C=CH), 2.44 (m, 4H, N(CH$_2$)$_2$), 2.01 (q, J=7.3 Hz, 2H, CH$_3$CH$_2$), 1.63 (s, 3H, CH$_3$C=CH), 0.97–1.04 (m, 3H, CH$_3$CH$_2$); $^{13}$C NMR (100 MHZ) δ141.1, 118.7, 67.0, 56.0, 53.5, 32.4, 16.4, 12.5; LRMS (FAB) m/z 169 (M)$^+$; HRMS (FAB) exact mass calcd for (C$_{10}$H$_{19}$NO)$^+$ requires m/z 169.1467, found m/z 169.1464. (b) Preparation of (2R*,3R*)-N-(2,3-Dimethyl-3-ethyl4-pentenoyl)-morpholine (18): Prepared according to general procedure B from (E)-N-(3-ethyl-3-methyl-2-propenyl)-morpholine 17 (135 mg, 0.80 mmol), TiCl$_4$.(THF)$_2$, (27 mg, 81 μmol), i-Pr$_2$NEt (0.56 mL, 3.2 mmol), and propionyl chloride (2.4 mL, 1 M solution in CH$_2$Cl$_2$, 2.4 mmol) in CH$_2$Cl$_2$ (2.7 mL) to provide the pure product as a yellow oil in 72% yield (130 mg, 0.58 mmol); >99:1 syn:anti. Syn isomer: IR (CH$_2$Cl$_2$) 2972, 1633, 1459, 1432, 1235 cm$^{-1}$; $^1$H NMR (400 MHZ) δ5.88 (dd, J=10.9 Hz, 17.6 Hz, 1H, CH=CH$_2$), 5.03 (dd, J=1.5, 10.9 Hz, 1H, CH=CH$_2$), 4.88 (dd, J=1.4, 17.6 Hz, 1H, CH=CH$_2$), 3.49–3.64 (m, 8H, N(CH$_2$CH$_2$)$_2$), 2.63 (q, J=6.9 Hz, 1H, CHC=O), 1.32–1.49 (m, 2H, CH$_2$CH$_3$), 1.02 (d, J=6.9 Hz, 3H, CH$_3$CHC=O), 0.99 (s, 3H, CHC$_3$C), 0.73 (t, J=7.5 Hz, 3H, CH$_3$CH$_2$); $^{13}$C NMR (100 MHZ) δ174.1, 143.8, 67.0, 66.7, 66.6, 46.8, 42.7, 42.2, 41.8, 30.9, 18.7, 13.3, 8.3; LRMS (FAB) m/z 225 (M)$^+$; HRMS (FAB) exact mass calcd for (C$_{13}$H$_{23}$NO2)$^+$ requires m/z 225.1710, found m/z 225.1727.

Examples 12 and 13 further illustrate the proficiency of the novel Claisen reaction to provide catalytic access to relatively elusive chemical structures. The principal issue in each of these reactions is that of transition state controlled π-facial discrimination to selectively build quaternary carbon stereocenters on both cyclic and acyclic structures. The reaction of propionyl chloride with 1-methyl-3-N-morpholino-cyclohexene (15) provides excellent levels of diastereocontrol in the formation of the quaternary carbon bearing cyclic adduct (16) (95:5 anti/syn). The reaction can also translate the subtle methyl versus ethyl substitution pattern on morpholine (17) to furnish the acyclic framework (18) with complete stereospecificity (>99:1 syn/anti).

We claim:
1. A method for conducting a Claisen rearrangement reaction, comprising reacting an allylic reactant with an acid chloride in the presence of a Lewis acid catalyst composition comprising a first catalyst component composed of a Lewis acid, and a second catalyst component selected from the group consisting of tertiary amines and non-nitrogenous bases.
2. The method of claim 1, wherein the allylic reactant is selected from the group consisting of allylic amines, allylic ethers and allylic thioethers.
3. The method of claim 2, wherein the allylic reactant is an allylic amine.
4. The method of claim 3, wherein the allylic reactant is an allylic tertiary amine.
5. The method of claim 1, wherein the acid chloride is a 2-substituted acetyl chloride.
6. The method of claim 1, wherein the molar ratio of the allylic reactant to the acid chloride is in the range of approximately 2:1 to 1:2.
7. The method of claim 1, wherein the molar ratio of the allylic reactant to the acid chloride is approximately 1:1.
8. The method of claim 1, wherein the reaction is carried out under inert, nonaqueous conditions.
9. The method of claim 1, wherein the reaction is carried out at a temperature in the range of approximately –110° C. to 200° C.
10. The method of claim 9, wherein the reaction is carried out at a temperature in the range of approximately –78° C. to 100° C.
11. The method of claim 1, wherein one of the allylic reactant, the acid chloride and the catalyst composition is covalently linked, either directly or indirectly, to the surface of a solid support.
12. The method of claim 1, wherein the size and/or positioning of substituents on the allylic reactant results in an enantioselective reaction.
13. The method of claim 1, wherein the second catalyst component is a tertiary amine.
14. The method of claim 1, wherein the second catalyst component is a non-nitrogenous base.
15. The method of claim 14, wherein the non-nitrogenous base is selected from the group consisting of inorganic hydroxides, inorganic oxides, and metal carbonates.
16. A method for synthesizing a compound having the structural formula (III)

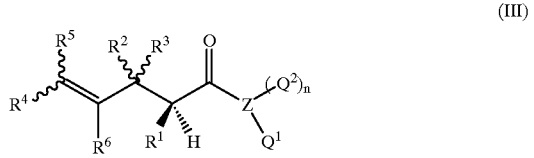

(III)

wherein R$^1$, R$^2$, R$^3$, R$^4$, R$^5$ and R$^6$ are independently selected from the group consisting of hydrido, halo, hydroxyl, sulfhydryl, amino, substituted amino, hydrocarbyl, substituted hydrocarbyl, heteroatom-containing hydrocarbyl, and substituted heteroatom-containing hydrocarbyl, Z is N, O or S, n is zero or 1, with the proviso that when Z is N, n is 1, and when Z is O or S, n is zero, and Q$^1$ and Q$^2$ are independently selected from the group consisting of hydrocarbyl, substituted hydrocarbyl, heteroatom-containing hydrocarbyl, and substituted heteroatom-containing hydrocarbyl, or, when Z is N and n is 1, Q$^1$ and Q$^2$ are joined together in a ring structure or together with Z form an azide group —N$_3$, the method comprising:

reacting an allylic reactant having the structure of formula (I)

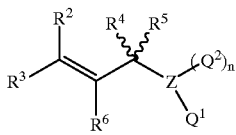
(I)

with an acid chloride having the structure of formula (II)

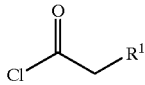
(II)

in the presence of a Lewis acid catalyst composition comprising a first catalyst component composed of a Lewis acid, and a second catalyst component selected from the group consisting of tertiary amines and non-nitrogenous bases.

17. A method for synthesizing a compound having the structural formula (IIIa)

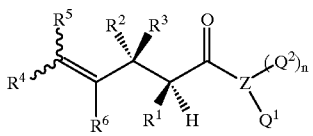
(IIIa)

wherein $R^1$, $R^2$, $R^3$, $R^4$, $R^5$ and $R^6$ are independently selected from the group consisting of hydrido, halo, hydroxyl, sulfhydryl, amino, substituted amino, hydrocarbyl, substituted hydrocarbyl, heteroatom-containing hydrocarbyl, and substituted heteroatom-containing hydrocarbyl, Z is N, O or S, n is zero or 1, with the proviso that when Z is N, n is 1, and when Z is O or S, n is zero, and $Q^1$ and $Q^2$ are independently selected from the group consisting of hydrocarbyl, substituted hydrocarbyl, heteroatom-containing hydrocarbyl, and substituted heteroatom-containing hydrocarbyl, or, when Z is N and n is 1, $Q^1$ and $Q^2$ are joined together in a ring structure or together with Z form an azide group —$N_3$, the method comprising:

reacting an allylic reactant having the structure of formula (Ia)

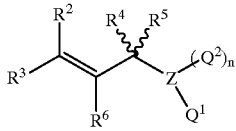
(Ia)

with an acid chloride having the structure of formula (II)

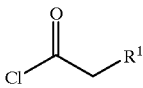
(II)

in the presence of a Lewis acid catalyst composition comprising a first catalyst component composed of a Lewis acid, and a second catalyst component selected from the group consisting of tertiary amines and non-nitrogenous bases.

18. A method for synthesizing a compound having the structural formula (IIIb)

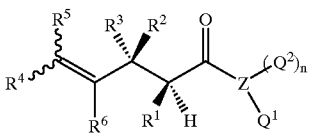
(IIIb)

wherein $R^1$, $R^2$, $R^3$, $R^4$, $R^5$ and $R^6$ are independently selected from the group consisting of hydrido, halo, hydroxyl, sulfhydryl, amino, substituted amino, hydrocarbyl, substituted hydrocarbyl, heteroatom-containing hydrocarbyl, and substituted heteroatom-containing hydrocarbyl, Z is N, O or S, n is zero or 1, with the proviso that when Z is N, n is 1, and when Z is O or S, n is zero, and $Q^1$ and $Q^2$ are independently selected from the group consisting of hydrocarbyl, substituted hydrocarbyl, heteroatom-containing hydrocarbyl, and substituted heteroatom-containing hydrocarbyl, or, when Z is N and n is 1, $Q^1$ and $Q^2$ are joined together in a ring structure or together with Z form an azide —$N_3$, the method comprising:

reacting an allylic reactant having the structure of formula (Ib)

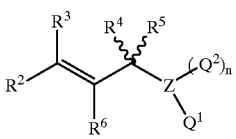
(Ib)

with an acid chloride having the structure of formula (II)

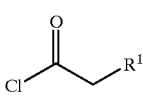
(II)

in the presence of a Lewis acid catalyst composition comprising a first catalyst component composed of a Lewis acid, and a second catalyst component composed of a tertiary amine.

19. A method for synthesizing a compound having the structural formula (IIIc)

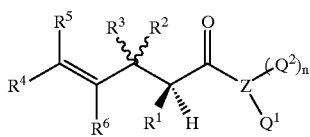
(IIIc)

wherein $R^1$, $R^2$, $R^3$, $R^4$, $R^5$ and $R^6$ are independently selected from the group consisting of hydrido, halo, hydroxyl, sulfhydryl, amino, substituted amino, hydrocarbyl, substituted hydrocarbyl, heteroatom-containing hydrocarbyl, and substituted heteroatom-containing hydrocarbyl, Z is N, O or S, n is zero or 1, with the proviso that when Z is N, n is 1, and when Z is O or S, n is zero, and with the further proviso that $R^4$ is a sterically bulky substituent relative to $R^5$, and $Q^1$ and $Q^2$ are independently selected from the group consisting of hydrocarbyl, substituted hydrocarbyl, heteroatom-containing hydrocarbyl, and substituted heteroatom-containing hydrocarbyl, or, when Z is N and n is 1, $Q^1$ and $Q^2$ are joined together in a ring structure or together with Z form an azide —$N_3$, the method comprising:

reacting an allylic reactant having the structure of formula (Ic)

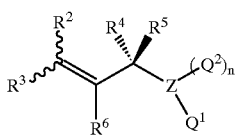
(Ic)

with an acid chloride having the structure of formula (II)

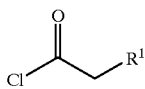
(II)

in the presence of a Lewis acid catalyst composition comprising a first catalyst component composed of a Lewis acid, and a second catalyst component selected from the group consisting of tertiary amines and non-nitrogenous bases.

20. A method for synthesizing a compound having the structural formula (IIId)

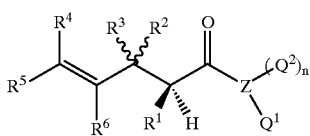
(IIId)

wherein $R^1$, $R^2$, $R^3$, $R^4$, $R^5$ and $R^6$ are independently selected from the group consisting of hydrido, halo, hydroxyl, sulfhydryl, amino, substituted amino, hydrocarbyl, substituted hydrocarbyl, heteroatom-containing hydrocarbyl, and substituted heteroatom-containing hydrocarbyl, Z is N, O or S, n is zero or 1, with the proviso that when Z is N, n is 1, and when Z is S, n is zero, and with the further proviso that $R^5$ is a sterically bulky substituent relative to $R^4$, and $Q^1$ and $Q^2$ are independently selected from the group consisting of hydrocarbyl, substituted hydrocarbyl, heteroatom-containing hydrocarbyl, and substituted heteroatom-containing hydrocarbyl, or, when Z is N and n is 1, $Q^1$ and $Q^2$ are joined together in a ring structure or together with Z form an azide —$N_3$, the method comprising:

reacting an allylic reactant having the structure of formula (Ic)

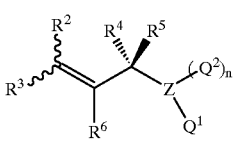
(Ic)

with an acid chloride having the structure of formula (II)

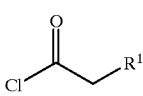
(II)

in the presence of a Lewis acid catalyst composition comprising a first catalyst component composed of a Lewis acid, and a second catalyst component selected from the group consisting of tertiary amines and non-nitrogenous bases.

21. The method of any one of claims 16, 17, 18, 19 and 20, wherein the first catalyst component has the structural formula (V)

$$M(X)_a(Y)_b \qquad (V)$$

wherein M is a metal, X is a halide, a halide-containing group, lower alkoxy, fluorinated lower alkoxy, sulfate, acetate, trifluoroacetate or triflate, Y is hydrocarbyl, substituted hydrocarbyl, heteroatom-containing hydrocarbyl, substituted heteroatom-containing hydrocarbyl, or an oxygen-containing or nitrogen-containing organic ligand, a is an integer of 1 or more, and the sum of a and b is in the range of 2 to $n_{max}$, where $n_{max}$ is the number of atoms that can bind to M through single covalent or coordination bonds.

22. The method of claim 21, wherein M is selected from the group consisting of Groups 2 through 13 of the Periodic Table of the Elements and lanthanides.

23. The method of claim 22, wherein M is selected from the group consisting of Ti, Mg, Al, Sc, Y, Ni, Cu, Zn and Yb.

24. The method of claim 23, wherein M is selected from the group consisting of Ti, Mg and Al.

25. The method of claim 21, wherein a is at least 2.

26. The method of claim 25, wherein X is a halide or triflate.

27. The method of claim 26, wherein Y is a nitrogen-containing ligand.

28. The method of claim 27, wherein Y has the structure of formula (VIa) or (VIb)

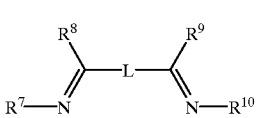
(VIa)

-continued

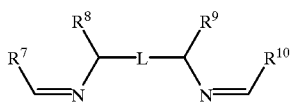
(VIb)

wherein L is a hydrocarbylene, substituted hydrocarbylene, heteroatom-containing hydrocarbylene, substituted heteroatom-containing hydrocarbylene or heteroatom linkage, and $R^7$, $R^8$, $R^9$ and $R^{10}$ are independently selected from the group consisting of hydrido, halo, hydroxyl, sulfhydryl, amino, substituted amino, hydrocarbyl, substituted hydrocarbyl, heteroatom-containing hydrocarbyl, and substituted heteroatom-containing hydrocarbyl, or wherein $R^7$ and $R^8$ and/or $R^9$ and $R^{10}$ may be linked to form a hydrocarbylene, substituted hydrocarbylene, heteroatom-containing hydrocarbylene, or substituted heteroatom-containing hydrocarbylene bridge.

29. The method of claim 28, wherein Y has the structure of formula (VIIa) or (VIIb)

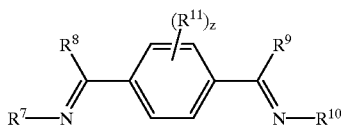
(VIIa)

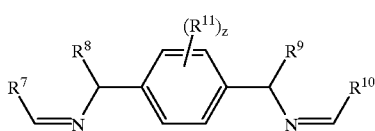
(VIIb)

wherein $R^{11}$ is as defined for $R^7$, $R^8$ and $R^9$, and z is an integer in the range of zero to 5 inclusive.

30. The method of claim 29, wherein Y has the structure of formula (VIIa).

31. The method of claim 30, wherein Y has the structure of formula (VIII)

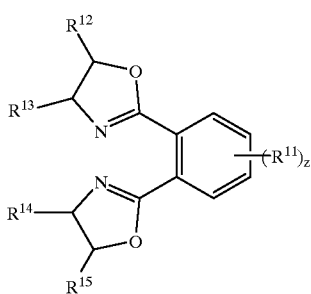
(VIII)

wherein $R^{12}$, $R^{13}$, $R^{14}$ and $R^{15}$ are defined as for $R^{11}$.

32. The method of any one of claims 16, 17, 18, 19 and 20, wherein the second catalyst component is a tertiary amine.

33. The method of claim 32, wherein the tertiary amine has the structure $NR^{16}R^{17}R^{18}$ wherein $R^{16}$, $R^{17}$ and $R^{18}$ are independently hydrocarbyl, substituted hydrocarbyl, heteroatom-containing hydrocarbyl or substituted heteroatom-containing hydrocarbyl, or wherein two of $R^{16}$, $R^{17}$ and $R^{18}$ are linked to form a hydrocarbylene, substituted hydrocarbylene, heteroatom-containing hydrocarbylene or substituted heteroatom-containing hydrocarbylene bridge.

34. The method of claim 33, wherein the tertiary amine is a trialkylamine.

35. The method of 34, wherein the tertiary amine is a tri(lower alkyl)amine.

36. The method of claim 32, wherein the tertiary amine is comprised of a nitrogen-containing heterocycle in which at least one nitrogen heteroatom is in the form —N=.

37. The method of any one of claims 16, 17, 18, 19 and 20, wherein the second catalyst component is a non-nitrogenous base.

38. The method of claim 37, wherein the non-nitrogenous base is selected from the group consisting of inorganic hydroxides, inorganic oxides, and metal carbonates.

39. The method of claim 38, wherein the non-nitrogenous base is selected from the group consisting of sodium hydroxide, potassium hydroxide, sodium carbonate and potassium carbonate.

40. The method of any one of claims 16, 17, 18, 19 and 20, wherein the molar ratio of the allylic reactant to the acid chloride is in the range of approximately 2:1 to 1:2.

41. The method of any one of claims 16, 17, 18, 19 and 20, wherein the reaction is carried out under inert, nonaqueous conditions.

42. The method of any one of claims 16, 17, 18, 19 and 20, wherein the reaction is carried out at a temperature in the range of approximately −110° C. to 200° C.

43. The method of claim 42, wherein the reaction is carried out at a temperature in the range of approximately −78° C. to 100° C.

44. The method of any one of claims 16, 17, 18, 19 and 20, wherein one of the allylic reactant, the acid chloride and the catalyst composition is covalently linked, either directly or indirectly, to the surface of a solid support.

* * * * *